United States Patent [19]

Basava et al.

[11] Patent Number: 5,554,728
[45] Date of Patent: Sep. 10, 1996

[54] LIPID CONJUGATES OF THERAPEUTIC PEPTIDES AND PROTEASE INHIBITORS

[75] Inventors: Channa Basava, San Diego; Karl Y. Hostetler, Del Mar, both of Calif.

[73] Assignee: NeXstar Pharmaceuticals, Inc., Boulder, Colo.

[21] Appl. No.: 734,434

[22] Filed: Jul. 23, 1991

[51] Int. Cl.⁶ .............................. C07K 5/00; C07K 7/00; C07K 17/00; A61K 38/00
[52] U.S. Cl. ................ 530/327; 530/328; 530/329; 530/330; 530/331; 530/345; 548/535; 562/561
[58] Field of Search ........................ 530/327–331, 530/345; 514/12–19; 548/535; 562/561

[56] References Cited

U.S. PATENT DOCUMENTS

| | | | |
|---|---|---|---|
| 5,086,165 | 4/1992 | Marshall et al. | 530/329 |
| 5,149,794 | 9/1992 | Yatvin et al. | 536/29 |
| 5,223,263 | 6/1993 | Hostetler et al. | 424/450 |
| 5,411,947 | 5/1995 | Hostetler et al. | 514/43 |

FOREIGN PATENT DOCUMENTS

| | | |
|---|---|---|
| 0342541 | 5/1988 | European Pat. Off. . |
| 0356223 | 8/1988 | European Pat. Off. . |
| 0357332 | 8/1988 | European Pat. Off. . |
| 0361341 | 9/1988 | European Pat. Off. . |
| 0365992 | 10/1988 | European Pat. Off. . |
| 0372537 | 12/1988 | European Pat. Off. . |
| 0373549 | 12/1988 | European Pat. Off. . |
| 0373576 | 12/1988 | European Pat. Off. . |
| 0387231 | 3/1989 | European Pat. Off. . |
| 0386611 | 3/1989 | European Pat. Off. . |
| 0337714 | 4/1989 | European Pat. Off. . |
| 0346847 | 6/1989 | European Pat. Off. . |
| 0354522 | 8/1989 | European Pat. Off. . |
| 2646353 | 4/1989 | France . |
| 3800233 | 2/1988 | Germany . |
| 3819846 | 6/1988 | Germany . |
| 3840452 | 12/1988 | Germany . |
| 3913272 | 4/1989 | Germany . |
| WO8809815 | 12/1988 | WIPO . |
| WO9012804 | 4/1989 | WIPO . |
| WO9101327 | 7/1989 | WIPO . |
| WO8910920 | 11/1989 | WIPO . |
| WO9000399 | 1/1990 | WIPO . |

OTHER PUBLICATIONS

Biochemical and Biophysical Research Communications, vol. 156, No. 1, issued Oct. 14, 1988, Darke et al., "HIV–1, protease specificity of peptide cleavage is sufficient for processing of GAG and POL polyproteins" pp. 297–303.
Merrifield, R., Solid–Phase Peptide Synthesis, *J. Chem. Soc.* 85:2149 (1963).
Blaug, S., *Remington's Pharmaceutical Sciences* 15th Ed.: Chapter 87 (1975).
Dreyer, G., et al., Inhibition of human immunodeficiency virus 1 protease in vitro . . . *Proc. Nat'l. Acad. Sci. USA* 86:9752–9756 (1989).
Meek, T. et al., Inhibition of HIV protease in infected T–lymphocites by synthetic peptide analogues. *Nature* 343:90–92 (1990).
McQuade, T. et al, A Synthetic HIV–1 protease inhibitor with antiviral activity arrests HIV–like particle maturation. *Science* 247:454–456 (1990).
Wlodawer, A., et al., Conserved Folding in Retroviral Proteases: Crystal Structure . . . *Research Articles* 245:616–621 (1989).
Marx, Jean L., NCI Team Remodels Key AIDS Virus Enzyme. *Science* 245:598 (1989).
Blundell, T. and Pearl, L., A second front against AIDS. *Nature* 337:596–597 (1989).

Primary Examiner—Toni R. Scheiner
Assistant Examiner—Sheela J. Huff
Attorney, Agent, or Firm—Swanson & Bratschun, LLC

[57] ABSTRACT

Compounds wherein therapeutic peptides are covalently linked to phospholipids, glycerides or other membrane-targeting and membrane-anchoring species, and their pharmaceutically acceptable salts, together with processes for their preparation. The targeting technology is applicable to HIV protease inhibitors and a variety of other enzyme inhibitors.

8 Claims, No Drawings

SEQUENCE LISTING ( 1 ) GENERAL INFORMATION:

( i i i ) NUMBER OF SEQUENCES: 35

( 2 ) INFORMATION FOR SEQ ID NO:1:

( i ) SEQUENCE CHARACTERISTICS:
                ( A ) LENGTH: 7 amino acids
                ( B ) TYPE: amino acid
                ( C ) STRANDEDNESS: single
                ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( i x ) FEATURE:
                ( A ) NAME/KEY: misc-difference
                ( B ) LOCATION: 7
                ( D ) OTHER INFORMATION: carboxyl group of terminal Val-7
                        residue is in amide form.

( x i ) SEQUENCE DESCRIPTION: SEQ ID NO:1:

Ser  Gly  Asn  Phe  Pro  Ile  Val
    1                        5

( 2 ) INFORMATION FOR SEQ ID NO:2:

( i ) SEQUENCE CHARACTERISTICS:
                ( A ) LENGTH: 7 amino acids
                ( B ) TYPE: amino acid
                ( C ) STRANDEDNESS: single
                ( D ) TOPOLOGY: linear ( i i ) MOLECULE TYPE: (A) peptide ( i i i ) HYPOTHETICAL: NO ( i v ) ANTI-SENSE: NO ( v ) FRAGMENT TYPE: internal ( i x ) FEATURE:
                ( A ) NAME/KEY: misc-difference
                ( B ) LOCATION: 7
                ( D ) OTHER INFORMATION: carboxyl group of terminal Val-7
                        residue is in amide form ( x i ) SEQUENCE DESCRIPTION: SEQ ID NO:2:

Ser  Gln  Asn  Tyr  Pro  Ile  Val
    1                        5

( 2 ) INFORMATION FOR SEQ ID NO:3:

( i ) SEQUENCE CHARACTERISTICS:
                ( A ) LENGTH: 7 amino acids
                ( B ) TYPE: amino acid
                ( C ) STRANDEDNESS: single
                ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( i x ) FEATURE:
    ( A ) NAME/KEY: Unusual amino acids; misc. differences
    ( B ) LOCATION: 5, 7
    ( D ) OTHER INFORMATION: Xaa=1- amino, 1-cyclohexane carboxylic acid (Achx); carboxyl group of terminal Val-7 residue is in amide form.

( x i ) SEQUENCE DESCRIPTION: SEQ ID NO:3:

Ser Gln Asn Tyr Xaa Ile Val
1               5

( 2 ) INFORMATION FOR SEQ ID NO:4:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( i x ) FEATURE:
    ( A ) NAME/KEY: Unusual amino acids; misc. differences
    ( B ) LOCATION: 5, 7
    ( D ) OTHER INFORMATION: Xaa=1- amino, 1-cyclopropane carboxylic acid (Acpr); carboxyl group of terminal Val-7 residue is in amide form.

( x i ) SEQUENCE DESCRIPTION: SEQ ID NO:4:

Ser Gln Asn Tyr Xaa Ile Val
1               5

( 2 ) INFORMATION FOR SEQ ID NO:5:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( i x ) FEATURE:
    ( A ) NAME/KEY: Unusual amino acids; misc. differences
    ( B ) LOCATION: 5, 7
    ( D ) OTHER INFORMATION: Xaa=1- amino, 1-cyclopentane carboxylic acid (Acpnt); carboxyl group of terminal Val-7 residue is in amide form.

( x i ) SEQUENCE DESCRIPTION: SEQ ID NO:5:

Ser Gln Asn Tyr Xaa Ile Val
1               5

( 2 ) INFORMATION FOR SEQ ID NO:6:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( i i ) MOLECULE TYPE: peptide (i i i) HYPOTHETICAL: NO (i v) ANTI-SENSE: NO (v) FRAGMENT TYPE: internal (i x) FEATURE:
    (A) NAME/KEY: Unusual amino acids; misc. differences
    (B) LOCATION: 4, 7
    (D) OTHER INFORMATION: Xaa=bAla; carboxyl group of
        terminal Arg-7 residue is in amide form.

(x i) SEQUENCE DESCRIPTION: SEQ ID NO:6:

Thr Ile Leu Xaa Leu Gln Arg
1               5

(2) INFORMATION FOR SEQ ID NO:7:

(i) SEQUENCE CHARACTERISTICS:
        (A) LENGTH: 13 amino acids
        (B) TYPE: amino acid
        (C) STRANDEDNESS: single
        (D) TOPOLOGY: linear (i i) MOLECULE TYPE: peptide (i i i) HYPOTHETICAL: NO (i v) ANTI-SENSE: NO (v) FRAGMENT TYPE: internal (i x) FEATURE:
        (A) NAME/KEY: Unusual amino acids; misc. differences
        (B) LOCATION: 10, 13
        (D) OTHER INFORMATION: Xaa=5- aminoisovaleric acid(Ava);
            carboxyl group of terminal Arg-13 residue is in amide
            form.

(x i) SEQUENCE DESCRIPTION: SEQ ID NO:7:

Ser Gln Asn Tyr Pro Ile Val Thr Leu Xaa Thr Gln Arg
1               5                       10

(2) INFORMATION FOR SEQ ID NO:8:

(i) SEQUENCE CHARACTERISTICS:
        (A) LENGTH: 6 amino acids
        (B) TYPE: amino acid
        (C) STRANDEDNESS: single
        (D) TOPOLOGY: linear (i i) MOLECULE TYPE: peptide (i i i) HYPOTHETICAL: NO (i v) ANTI-SENSE: NO (v) FRAGMENT TYPE: internal (i x) FEATURE:
        (A) NAME/KEY: Unusual amino acids; misc. differences
        (B) LOCATION: 1, 3, 4, 5, 6
        (D) OTHER INFORMATION: Xaa3 =phenylalanine (Phe);
            Xaa4=4- piperidine carboxylic acid (Pip); Xaa5 =
            $\alpha$ - hydroxyleucine($\alpha$-OH—Leu); amino group of initial Ala-1
            residue is acetylated; carboxyl group of terminal Val-6
            residue is in amide form.

(x i) SEQUENCE DESCRIPTION: SEQ ID NO:8:

Ala Ala Xaa Xaa Xaa Val
1               5

(2) INFORMATION FOR SEQ ID NO:9:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( i x ) FEATURE:
    ( A ) NAME/KEY: Unusual amino acids; misc. differences
    ( B ) LOCATION: 4, 7
    ( D ) OTHER INFORMATION: Xaa: βalanine(bAla);
        terminal Gly-7 residue is hydroxylated.

( x i ) SEQUENCE DESCRIPTION: SEQ ID NO:9:

Ala Ala Phe Xaa Val Val Gly
1               5

( 2 ) INFORMATION FOR SEQ ID NO:10:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( i x ) FEATURE:
    ( A ) NAME/KEY: Unusual amino acids; misc. differences
    ( B ) LOCATION: 4, 5, 7
    ( D ) OTHER INFORMATION: Xaa4=bAla; Xaa5=Nva
        carboxy terminal Gly-7 residue is hydroxylated.

( x i ) SEQUENCE DESCRIPTION: SEQ ID NO:10:

Ala Ala Phe Xaa Xaa Val Gly
1               5

( 2 ) INFORMATION FOR SEQ ID NO:11:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( i x ) FEATURE:
    ( A ) NAME/KEY: Unusual amino acids; misc. differences
    ( B ) LOCATION: 4, 5, 7
    ( D ) OTHER INFORMATION: Xaa4=bAla; Xaa5=α-OH-isovaleryl;
        carboxy terminal Gly-7 residue is hydroxylated.

( x i ) SEQUENCE DESCRIPTION: SEQ ID NO:11:

Ala Ala Phe Xaa Xaa Val Gly 1          5

(2) INFORMATION FOR SEQ ID NO:12:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
        (A) NAME/KEY: Unusual amino acids; misc. differences
        (B) LOCATION: 4, 7
        (D) OTHER INFORMATION: Xaa: βalanine(bAla);
            carboxy terminal Gly-7 residue is a methyl ester.

(xi) SEQUENCE DESCRIPTION: SEQ ID NO:12:

Ala  Ala  Phe  Xaa  Val  Val  Gly
1                       5

(2) INFORMATION FOR SEQ ID NO:13:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
        (A) NAME/KEY: Unusual amino acids; misc. differences
        (B) LOCATION: 4, 5, 7
        (D) OTHER INFORMATION: Xaa4=bAla; Xaa5=Nva
            carboxy terminal Gly-7 residue is a methyl ester.

(xi) SEQUENCE DESCRIPTION: SEQ ID NO:13:

Ala  Ala  Phe  Xaa  Xaa  Val  Gly
1                       5

(2) INFORMATION FOR SEQ ID NO:14:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
        (A) NAME/KEY: Unusual amino acids; misc. differences
        (B) LOCATION: 4, 5, 7
        (D) OTHER INFORMATION: Xaa4=bAla; Xaa5=α-OH-isovaleryl;
            carboxy terminal Gly-7 residue is a methyl ester.

( x i ) SEQUENCE DESCRIPTION: SEQ ID NO:14:

Ala Ala Phe Xaa Xaa Val Gly
1               5

( 2 ) INFORMATION FOR SEQ ID NO:15:

( i ) SEQUENCE CHARACTERISTICS:
      ( A ) LENGTH: 6 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( i x ) FEATURE:
      ( A ) NAME/KEY: Unusual amino acids; misc. differences
      ( B ) LOCATION: 4, 5, 6
      ( D ) OTHER INFORMATION: Xaa4=bAla; Xaa5=norvaline(Nva);
          amino terminal Ala-1 residue is modified by
          t- butyloxycarbonyl attached to amino group; terminal
          Gly-6 residue is a methyl ester.

( x i ) SEQUENCE DESCRIPTION: SEQ ID NO:15:

Ala Ala Phe Xaa Xaa Gly
1               5

( 2 ) INFORMATION FOR SEQ ID NO:16:

( i ) SEQUENCE CHARACTERISTICS:
      ( A ) LENGTH: 4 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( i x ) FEATURE:
      ( A ) NAME/KEY: Unusual amino acids; misc. differences
      ( B ) LOCATION: 3, 4
      ( D ) OTHER INFORMATION: Xaa3=L-α- naphthylalanine(L-α-Nal);
          Xaa4=4- piperidine carboxylic acid (Pip); initial amino
          terminal Ala-1 residue is an acetamide; carboxy terminal
          pipecolic acid, Pip-7, is a methyl ester.

( x i ) SEQUENCE DESCRIPTION: SEQ ID NO:16:

Ala Ala Xaa Xaa
1

( 2 ) INFORMATION FOR SEQ ID NO:17:

( i ) SEQUENCE CHARACTERISTICS:
      ( A ) LENGTH: 4 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( i x ) FEATURE:
    ( A ) NAME/KEY: Unusual amino acids; misc. differences
    ( B ) LOCATION: 3, 4
    ( D ) OTHER INFORMATION: Xaa3=L-α- naphthylalanine(L-α-Nal);
        Xaa4=4- piperidine carboxylic acid (Pip); initial amino
        terminal Ala-1 residue is an acetamide; carboxy terminal
        pipecolic acid, Pip-4, is a hydrazide.

( x i ) SEQUENCE DESCRIPTION: SEQ ID NO:17:

Ala  Ala  Xaa  Xaa
1

( 2 ) INFORMATION FOR SEQ ID NO:18:

( i ) SEQUENCE CHARACTERISTICS:
    ( A ) LENGTH: 4 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( i x ) FEATURE:
    ( A ) NAME/KEY: Unusual amino acids; misc. differences
    ( B ) LOCATION: 3, 4
    ( D ) OTHER INFORMATION: Xaa3=L-α- naphthylalanine(L-α-Nal);
        Xaa4=4- piperidine carboxylic acid (Pip); amino terminal
        Ala-1 residue is a cholic amide; carboxy terminal
        pipecolic acid, Pip-4 is a methyl ester.

( x i ) SEQUENCE DESCRIPTION: SEQ ID NO:18:

Ala  Ala  Xaa  Xaa
1

( 2 ) INFORMATION FOR SEQ ID NO:19:

( i ) SEQUENCE CHARACTERISTICS:
    ( A ) LENGTH: 4 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( i x ) FEATURE:
    ( A ) NAME/KEY: Unusual amino acids; misc. differences
    ( B ) LOCATION: 3, 4
    ( D ) OTHER INFORMATION: Xaa3=L-α- naphthylalanine(L-α-Nal);
        Xaa4=4- piperidine carboxylic acid (Pip); initial amino
        terminal Ala-1 residue is a cholic amide; carboxy
        terminal pipecolic acid, Pip-4, is a hydrazide.

( x i ) SEQUENCE DESCRIPTION: SEQ ID NO:19:

Ala  Ala  Xaa  Xaa
1

( 2 ) INFORMATION FOR SEQ ID NO:20:

( i ) SEQUENCE CHARACTERISTICS:

( A ) LENGTH: 8 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( i x ) FEATURE:
    ( A ) NAME/KEY: Unusual amino acids; misc. differences
    ( B ) LOCATION: 8
    ( D ) OTHER INFORMATION: carboxy terminal Val-8 residue is
        an amide.

( x i ) SEQUENCE DESCRIPTION: SEQ ID NO:20:

Val Ser Gln Asn Tyr Pro Ile Val
1               5

( 2 ) INFORMATION FOR SEQ ID NO:21:

( i ) SEQUENCE CHARACTERISTICS:
    ( A ) LENGTH: 4 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( i x ) FEATURE:
    ( A ) NAME/KEY: Unusual amino acids; misc. differences
    ( B ) LOCATION: 3, 4
    ( D ) OTHER INFORMATION: Xaa=4- piperidine carboxylic
        acid(Pip); Phe-2 is joined to Xaa by an isosteric bond
        having the structure —C(O)—CH2—N—; carboxy terminal
        Ile-4 is an amide.

( x i ) SEQUENCE DESCRIPTION: SEQ ID NO:21:

Asn Phe Xaa Ile
1

( 2 ) INFORMATION FOR SEQ ID NO:22:

( i ) SEQUENCE CHARACTERISTICS:
    ( A ) LENGTH: 4 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( i x ) FEATURE:
    ( A ) NAME/KEY: Unusual amino acids; misc. differences
    ( B ) LOCATION: 2-3, 3, 4
    ( D ) OTHER INFORMATION: Xaa=4- piperidine carboxylic acid
        ( P i p ); Phe-2 is joined to Xaa by an isosteric link having
        the structure —C(O)—CH2—N—; amino terminal Asn-1 residue
        is a quinoloyl derivative; carboxy terminal Ile-4 is an
        amide.

( x i ) SEQUENCE DESCRIPTION: SEQ ID NO:22:

Asn Phe Xaa Ile
1

( 2 ) INFORMATION FOR SEQ ID NO:23:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( i x ) FEATURE:
        ( A ) NAME/KEY: Unusual amino acids; misc. differences
        ( B ) LOCATION: 6, 9
        ( D ) OTHER INFORMATION: Xaa=4- piperidine carboxylic acid
        ( P i p ); carboxy terminal Gln-9 residue is an amide.

( x i ) SEQUENCE DESCRIPTION: SEQ ID NO:23:

Val Ser Gln Asn Tyr Xaa Ile Val Gln
1                             5

( 2 ) INFORMATION FOR SEQ ID NO:24:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( i x ) FEATURE:
        ( A ) NAME/KEY: Unusual amino acids; misc. differences
        ( B ) LOCATION: 3, 6
        ( D ) OTHER INFORMATION: Xaa=decahydroisoquinoline
                carboxylic acid (Diq); Phe-2 is joined to Xaa by an
                isosteric link having the structure —CHOH—CH2—N—;
                amino terminal Asn-1 residue is a quinoloyl derivative;
                carboxy terminal Gln-6 is an amide.

( x i ) SEQUENCE DESCRIPTION: SEQ ID NO:24:

Asn Phe Xaa Ile Val Gln
1                  5

( 2 ) INFORMATION FOR SEQ ID NO:25:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( i x ) FEATURE:
    ( A ) NAME/KEY: Unusual amino acids; misc. differences
    ( B ) LOCATION: 6, 9
    ( D ) OTHER INFORMATION: Xaa=decahydroisoquinoline
        carboxylic acid (Diq); carboxy terminal Gln-9 residue is
        an amide.

( x i ) SEQUENCE DESCRIPTION: SEQ ID NO:25:

Val Ser Gln Asn Tyr Xaa Ile Val Gln
1               5

( 2 ) INFORMATION FOR SEQ ID NO:26:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( i x ) FEATURE:
        ( A ) NAME/KEY: misc-difference
        ( B ) LOCATION: 1, 7
        ( D ) OTHER INFORMATION: amino terminal Ser-1 is a succinyl
        derivative; carboxyl group of terminal Val-7 residue is
        in amide form.

( x i ) SEQUENCE DESCRIPTION: SEQ ID NO:26:

Ser Gly Asn Tyr Pro Ile Val
1               5

( 2 ) INFORMATION FOR SEQ ID NO:27:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( i x ) FEATURE:
        ( A ) NAME/KEY: misc-difference
        ( B ) LOCATION: 1
        ( D ) OTHER INFORMATION: amino terminal Ser-1 is a succinyl
        derivative.

( x i ) SEQUENCE DESCRIPTION: SEQ ID NO:27:

Ser Gly Asn Tyr
1

( 2 ) INFORMATION FOR SEQ ID NO:28:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( i x ) FEATURE:
    ( A ) NAME/KEY: Unusual amino acids; misc. differences
    ( B ) LOCATION: 1, 3, 4
    ( D ) OTHER INFORMATION: Xaa=4- piperidine carboxylic acid
        ( P i p ); Phe is joined to Xaa by an isosteric link having
        the structure —CHOH—CH2—N—; amino terminal Asn-1 residue
        is a quinoloyl derivative; carboxy terminal Ile-4 is an
        amide.

( x i ) SEQUENCE DESCRIPTION: SEQ ID NO:28:

Asn Phe Xaa Ile
1

( 2 ) INFORMATION FOR SEQ ID NO:29:

( i ) SEQUENCE CHARACTERISTICS:
    ( A ) LENGTH: 4 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( i x ) FEATURE:
    ( A ) NAME/KEY: Misc. differences
    ( B ) LOCATION: 1-2, 4
    ( D ) OTHER INFORMATION: Phe-1 is joined to Phe-2 by an
        isosteric linkage having the structure —CHOH—CH2—N—;
        carboxy terminal Ile-4 is an amide.

( x i ) SEQUENCE DESCRIPTION: SEQ ID NO:29:

Phe Phe Ile Phe
1

( 2 ) INFORMATION FOR SEQ ID NO:30:

( i ) SEQUENCE CHARACTERISTICS:
    ( A ) LENGTH: 4 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( i x ) FEATURE:
    ( A ) NAME/KEY: Misc. differences
    ( B ) LOCATION: 1-2, 4
    ( D ) OTHER INFORMATION: Phe-1 is joined to Phe-2 by an
        isosteric linkage having the structure —CHOH—CH2—N—;
        carboxy terminal Val-4 is an amide.

( x i ) SEQUENCE DESCRIPTION: SEQ ID NO:30:

Phe Pro Ile Val
1

( 2 ) INFORMATION FOR SEQ ID NO:31:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( i x ) FEATURE:
        ( A ) NAME/KEY: Unusual amino acids; misc. differences
        ( B ) LOCATION: 7, 10, 11
        ( D ) OTHER INFORMATION: Xaa7=4- NO2 phenylalanine(4-NO2—
            Phe); Xaa10=norleucine(Nle); carboxy terminal Ser-11 is
            an amide.

( x i ) SEQUENCE DESCRIPTION: SEQ ID NO:31:

```
His Lys Arg Ala Val Leu Xaa Glu Ala Xaa Ser
 1               5                   10
```

( 2 ) INFORMATION FOR SEQ ID NO:32:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( i x ) FEATURE:
        ( A ) NAME/KEY: Misc. differences
        ( B ) LOCATION: 1, 1-2, 4
        ( D ) OTHER INFORMATION: amino terminal Phe-1 residue is a
            t- butyloxycarbonyl derivative; Phe-1 and Phe-2 are joined
            by an isosteric link having the structure —CHOH—CH2—N—;
            carboxy terminal Phe-4 is an amide.

( x i ) SEQUENCE DESCRIPTION: SEQ ID NO:32:

```
Phe Phe Ile Phe
 1
```

( 2 ) INFORMATION FOR SEQ ID NO:33:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( i x ) FEATURE:
        ( A ) NAME/KEY: Unusual amino acids; misc. differences
        ( B ) LOCATION: 1, 1-2, 4
        ( D ) OTHER INFORMATION: amino terminal Ala-1 residue is a
            t- butyloxycarbonyl derivative; Phe-1 and Pro-2 are joined by an isosteric link having the structure —CHOH—CH2—N—;
carboxy terminal Val-4 is an amide.

(xi) SEQUENCE DESCRIPTION: SEQ ID NO:33:

Phe Pro Ile Val
1

(2) INFORMATION FOR SEQ ID NO:34:

(i) SEQUENCE CHARACTERISTICS:
  (A) LENGTH: 4 amino acids
  (B) TYPE: amino acid
  (C) STRANDEDNESS: single
  (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
  (A) NAME/KEY: Unusual amino acids; misc. differences
  (B) LOCATION: 1, 4
  (D) OTHER INFORMATION: amino terminal Phe-1 residue is
      modified by succinyl attached to amino group; carboxy
      terminal Phe-4 is an amide.

(xi) SEQUENCE DESCRIPTION: SEQ ID NO:34:

Phe Phe Ile Phe
1

(2) INFORMATION FOR SEQ ID NO:35:

(i) SEQUENCE CHARACTERISTICS:
  (A) LENGTH: 4 amino acids
  (B) TYPE: amino acid
  (C) STRANDEDNESS: single
  (D) TOPOLOGY: linear (ii) MOLECULE TYPE: peptide (iii) HYPOTHETICAL: NO (iv) ANTI-SENSE: NO (v) FRAGMENT TYPE: internal (ix) FEATURE:
  (A) NAME/KEY: Misc. differences
  (B) LOCATION: 1, 4
  (D) OTHER INFORMATION: amino terminal Tyr-1 residue is
      modified by t-butyloxycarbonyl attached to amino group;
      carboxy terminal Gly-4 is hydroxylated.

(xi) SEQUENCE DESCRIPTION: SEQ ID NO:35:

Tyr Pro Ile Gly
1

LIPID CONJUGATES OF THERAPEUTIC PEPTIDES AND PROTEASE INHIBITORS

This invention provides lipid conjugates of therapeutic peptides. It also provides peptide inhibitors of HIV protease.

BACKGROUND OF THE INVENTION

The uptake of therapeutic peptides into cells following in vivo administration is not efficient. A substantial amount of peptides are removed extremely rapidly from the plasma by a variety of mechanisms including cellular uptake and metabolism, filtration by the kidney and urinary excretion or destruction by the proximal tubule cells of the kidney. Furthermore the lipid bilayer of the cell membrane presents a barrier to transport. Yet another disadvantage of these peptides is the need to administer them by injection because peptides in general possess very poor oral or nasal bioavailability.

The human immunodeficiency virus (HIV) produces a long gag polyprotein which is cleaved during viral budding into smaller proteins which have specific viral functions. This proteolytic cleavage is catalyzed by a specific HIV aspartyl protease enzyme (HIV PR). Small peptide fragments which conformationally resemble the HIV protease binding site but have the p1 site replaced by non-hydrolyzable structures act as inhibitors of the HIV protease and may be useful as therapeutic agents in AIDS.

A number of such protease inhibitors have been synthesized. See for example, Merck European Patent Application # EP 0 337 714 A, publications by Upjohn, *Science* 247:454–456 (1990), Roche European Patent Application EP 0 346 847 A2, Smith, Kline French International Patent Application WO 90/00399, *Nature* 343:90–92 (1990), *Proc. Natl. Acad Sci.USA* 86:9752–9756 (1989), Hoechst European patent Application EP 0 354 522 A1. All of these protease-inhibitors are peptides, and as peptides, are subject to a general problem of metabolic degradation and clearance which will prevent them from reaching the infected cell targets to bind HIV PR.

Protease inhibitory peptides, as well as other therapeutic peptides, lack targeting mechanisms in their native form, and on administration to an animal they become distributed globally. For that reason they may not effectively treat infected tissues. For example, macrophages are believed to be a major site of HIV infection, and inhibitory peptides by themselves do not target to the macrophage reservoir.

These problems can be overcome by preparing conjugates of therapeutic peptides which resist clearance and degradation, and which can be targeted to the cell.

It is therefore the object of the invention to overcome the problem of degradation and clearance of therapeutic peptides, including HIV protease inhibitory peptides, from the plasma. It is further the object of the invention to provide peptides comprising nonhydrolyzable groups capable of inhibiting HIV PR. Another object of this invention is to provide for prodrugs of protease inhibitory peptides which treat the site of viral infection effectively. Yet another object of this invention is to improve the oral and nasal bioavailability of therapeutic peptides.

SUMMARY OF THE INVENTION

The invention provides peptide-lipid linking structures, protease inhibitors, and compounds wherein protease inhibitors and other therapeutic peptides are covalently linked to phospholipids, glycerides or other cell membrane targeting or membrane anchoring moieties.

According to one aspect of the invention there are provided therapeutic peptides which are analogues of substrates for proteases. These peptides include the protease substrates of Group I described in detail in the specification. Preferred peptides of this group inhibit the HIV protease.

According to another aspect of the invention there are provided compounds capable of linking peptides to lipid structures. These linking compounds include the amino acid phospholipids of Group IIA-D described in the specification, as well as other lipid-bearing linkers defined as X species, suitable for attachment to an amino group of a peptide and C species, suitable for attachment to the carboxyl group of a peptide.

According to yet another aspect of the invention there are provided peptide-lipid conjugates, comprising therapeutic peptides conjugated to any of the lipid-bearing linkers defined by the invention. Preferred species are lipid derivatives of protease inhibitory peptides. The peptide lipid conjugates can also comprise spacers, comprising bifunctional alkyl groups defined as Y, Z, and W species, which can modulate the distance between the peptide and the lipid linker. Preferred peptide-lipid conjugates comprise peptides that are protease inhibitors. These conjugates of Group III-A–F are described in detail in the specification.

The invention also provides intermediate compounds useful in the synthesis of the peptide-lipid compounds of the invention, comprising derivatized linking compounds suitable for binding to the functional groups of lipids or peptides.

The invention also provides a method for synthesizing peptide-lipid conjugates, comprising the steps of selecting a therapeutic peptide having an available amino group or carboxyl group; chemically bonding a bivalent linker group to either the amino or the carboxyl group; and chemically bonding a lipid species to the linker. In a preferred method, the peptide is a protease inhibitor.

The invention further provides a method of treating infectious disease caused by a virus, comprising administering to the infected person an effective virus-inhibiting amount of a lipid derivative of a viral protease inhibitory peptide. The inhibitory peptide-lipid can be incorporated into a liposome prior to administration. In a preferred embodiment of the method, the disease treated is HIV infection, and the peptide is a HIV protease inhibitor.

DETAILED DESCRIPTION OF THE INVENTION

The invention provides protease inhibitory peptides, lipid conjugates of therapeutic peptides, particularly peptides that are enzyme substrates, such as the HIV protease inhibitory peptides, linkers capable of attaching lipid species to the peptides, intermediate compounds, and methods of synthesis and use.

Group I: Protease inhibitors:

Protease inhibitors (PIs) are, in general, substrates of HIV 1 protease in which the amino acid residues at the p1 site are replaced by isosteric residues. Some of the HIV protease substrates which are the basis for the design of PIs are:

| Sequence | Site |
| --- | --- |
| Ser—Gln—Asn—Tyr—Pro—Ile—Val | p17/p24 |
| Ala—Arg—Val—Leu—Ala—Glu—Ala | p24/p7 |
| Ala—Thr—Ile—Met—Met—Gln—Arg | p24/p7 |
| Ser—Phe—Asn—Phe—Pro—Gln—Ile | HIV PR N-term |

Detailed descriptions of the design and structures of individual PIs are discussed below. The present invention provides for the following PIs:

Ser-Gln-Asn-Phe-Pro-Ile-Val-NH$_2$;
Ser-Gln-Asn-Tyr-Pro-Ile-Val-NH$_2$;
Ser-Gln-Asn-Tyr-Achx-Ile-Val-NH$_2$;
Ser-Gln-Asn-Tyr-Acpr-Ile-Val-NH$_2$;
Ser-Gln-Asn-Tyr-Acpnt-Ile-Val-NH$_2$;
Thr-Ile-Leu-(beta-Ala)-Leu-Gln-Arg-NH$_2$;
Ser-Gln-Asn-Tyr-Pro-Ile-Val-Thr-Leu-Ava-Thr-Gln-Arg-NH$_2$
Ac-Ala-Ala-(D-a-Nal)-Pip-(a-(OH)-Leu)-Val-NH$_2$;
Ac-Ala-Ala-Phe-Pip-(a-(OH)-Leu)-Val-NH$_2$;
Ac-Ala-Ala-(DL-Phe(4-Cl))-Pip-(a-(OH)-Leu)-Val-NH$_2$;
Ala-Ala-Phe-(beta-Ala)-Val-Val-Gly-OH;
Ala-Ala-Phe-(beta-Ala)-Nva-Val-Gly-OH;
Ala-Ala-Phe-(beta-Ala)-(a-(OH)-iso-Valeryl)-Val-Gly-OH;
Ala-Ala-Phe-(beta-Ala)-Val-Val-Gly-OMe;
Ala-Ala-Phe-(beta-Ala)-Nva-Val-Gly-OMe;
Ala-Ala-Phe-(beta-Ala)-(a-(OH)-iso-Valeryl)-Val-Gly-OMe;
Boc-Ala-Ala-Phe-(beta-Ala)-Nva-Gly-OMe;
(a,e-di-Myristoyl-Lys)-D-Pro-Ava-Ala-Phe-Ava-Val-Gly-OMe
Ac-Ala-Ala-(D-a-Nal)-Pip-OMe;
Ac-Ala-Ala-(D-a-Nal)-Pip-NHNH$_2$;
Ac-Ala-Ala-(L-a-Nal)-Pip-OMe;
Ac-Ala-Ala-(L-a-Nal)-Pip-NHNH$_2$;
Ac-Ala-Ala-(D-b-Nal)-Pip-OMe;
Ac-Ala-Ala-(D-b-Nal)-Pip-NHNH$_2$;
Chl-Ala-Ala-(L-a-Nal)-Pip-OMe;
Chl-Ala-Ala-(L-a-Nal)-Pip-NHNH$_2$;
Paa-Ala-Ala-(D-a-Nal)-Pip-OMe;
Ac-Ala-Ala-(DL-Phe(4-Cl))-Pip-OH;
Val-Ser-Gln-Asn-Tyr-Pro-Ile-Val-NH$_2$;
Val-Ser-Gln-Asn-(D-a-Nal)-Pip-(a-(OH)-Leu)-Val-NH$_2$;
i-Boc-(D-Phe)-(D-a-Nal)-Pip-(a-(OH)-Leu)-Val-NH$_2$;
(i-Boc-(D-Phe)-Leu-)$_2$-(3,5-di-Aba)-Pro-Leu-(D-Phe)-NH$_2$;
(Myristoyl-(D-Phe)-Leu-)$_2$-(3,5-di-Aba)-Pro-Leu-(D-Phe)-NH$_2$;
i-Boc-(3,5-di-Aba)-(D-a-Nal)-Pip-(a-(OH)-Leu)-Val-NH$_2$;
Pro-Ile-Val-NH$_2$;
Asn-Phe(CO—CH$_2$N)Pip-Ile-NH$_2$;
Quinaldoyl-Asn-Phe(CO—CH$_2$N)Pip-Ile-NH$_2$;
Val-Ser-Gln-Asn-Tyr-Pip-Ile-Val-Gln-NH$_2$;
Quinaldoyl-Asn-Phe(CHOH—CH$_2$N)Diq-Ile-Val-Gln-NH$_2$;
Val-Ser-Gln-Asn-Tyr-Diq-Ile-Val-Gln-NH$_2$;
Boc-Asn-Phe(CO—CH$_2$N)-Diq-NHtBu;
Succinyl-Ser-Gln-Asn-Tyr-Pro-Ile-Val-NH$_2$;
Succinyl-Ser-Gln-Asn-Tyr;
Quinaldoyl-Asn-Phe(CHOH—CH$_2$N)Pip-Ile-NH$_2$;
Phe(CHOH—CH$_2$N)Phe-Ile-Phe-NH$_2$;
Phe(CHOH—CH$_2$N)Pro-Ile-Val-NH$_2$;
His-Lys-Arg-Ala-Val-Leu-Phe(4-NO$_2$)-Glu-Ala-Nle-Ser-NH$_2$;
[D-Phe]-[D-a-Nal]-Pip-[L-a-(OH)-Leu]-Val-NH$_2$;
Boc-Phe(CHOH—CH$_2$N)Phe-Ile-Phe-NH$_2$;
Boc-Phe(CHOH—CH$_2$N)Pro-Ile-Val-NH$_2$;
Succinyl-Phe(CHOH—CH$_2$N)Phe-Ile-Phe-NH$_2$;
[D-Phe]-[D-b-Nal]-Pip-[L-a-(OH)-Leu]-Val-NH$_2$;
i-Boc-Tyr-Pro-Ile-Gly-OH;
(Boc-Phe-O-CH$_2$—CHOH)$_2$;
(Boc-Val-Phe-O—CH$_2$—CHOH)$_2$;
(Boc-Ser-Phe-O—CH$_2$—CHOH)$_2$;
(Boc-Asn-Phe-O—CH$_2$—CHOH)$_2$; and
(Boc-Arg-Phe-O—CH$_2$—CHOH)$_2$.

Lipid bearing Linkers

The invention also provides a means for improving the usefulness, efficacy, biological half life, transport across cellular membrane, oral and or nasal bioavailabilities of therapeutic peptides, including viral protease inhibitors by conjugating them to lipids via ester, amide, phosphate or phosphodiester bonds.

The protease inhibitory peptides of the invention, as well as other therapeutic peptides, can be derivatized with groups which help to increase their plasma half life and protect against tissue and renal clearance. By selecting suitable anchoring groups, that is membrane seeking, lipid associating groups, one can achieve selective targeting of the peptide or protease inhibitor. A number of natural and synthetic molecules such as glycolipids, phospholipids, fatty acids, diglycerides, and lipid associating groups such as cholesterol, lend themselves as candidates for anchoring the protease inhibitors to the lipid bilayer of cell membranes.

Furthermore, the linkage between the anchoring group and the peptide or protease inhibitor can be modulated in such a way as to obtain optimum rate of release of the drug or to position the drug in the most suitable conformation. These modified analogues of the viral protease inhibitory peptides may then be incorporated into liposomes, administered by injection (subcutaneously, intravenously, intraperitoneally or intramuscularly) to an animal. The derivatized peptides in liposomes will then have a much longer time of retention in the plasma; and will survive to be delivered to macrophages, a major site of HIV infection. In addition it can be expected that the lymphocyte reservoir of the HIV infection will also receive a larger amount of the lipid-modified peptide by virtue of its ability to undergo exchange and transfer to the surface membranes of cells in the circulation, such as the CD4+ lymphocytes. Finally, this approach will also be usefully applied to other protease inhibitory peptides, such as those for renin.

In order to prepare peptide-lipid conjugates, a number of linker groups were designed. They offer a convenient way of conjugating lipids, phospholipids, fatty acids, or glycerides to small peptides or protease inhibitors. These linkers are designed to take advantage of natural biochemical processes to release the active drug at or near the site of enzyme action thus imparting improved biological functions to the parent drug. A number of molecules containing multiple functional groups are suitable these linkers.

Particularly suitable for use as linkers are the amino acids having hydroxyl functional groups. These hydroxyamino acids are attached to phosphate or the phosphate group of phospholipids through a phosphoester bond between the phosphate group and the amino acid hydroxyl, thus leaving both characteristic amino acid groups, the amino acid NH$_2$, and the amino acid COOH, available to attach to the peptide carboxyl and amino groups, respectively, through amide bonds. Hydroxyamino acid phosphates can be attached to diacyl, dialkyl, monoacyl or monoalkyl glycerols to provide peptides linked to lipids via a monophosphate bond. Phosphatidyltyrosine, phosphatidyl-serine, phosphatidyl-threonine, and phosphatidyl-hydroxyproline are some examples of preferred linkers. In a similar manner diacyl, dialkyl, monoacyl or monoalkyl phospholipids could also be attached to the phosphatidyl-hydroxyamino acids to furnish peptides linked to lipids through a diphosphate bond.

The following linker moieties are preferred for preparing the peptide-lipid conjugates:

Group II: Lipid-bearing Linker compounds

The invention provides phospholipid-amino acid compounds, having the phosphoester bond described above, wherein the phospholipid comprises one or two linear or branched $C_4$–$C_{24}$ alkyl chains, each chain having from 0 to 6 double bonds. $C_{12}$–$C_{18}$ alkyl chains are preferred, and those having an even number of carbon atoms particularly preferred. The alkyl chains can be attached by means of the hydroxyl groups of the glyceryl portion of the phospholipid in 1,2 -diradyl form, that is through acyl/acyl acyl/alkyl alkyl/acyl or alkyl/alkyl bonds. Alternatively, the phospholipid may be a lyso species, having only one alkyl chain.

Accordingly, preferred species of lipid bearing linkers are:

Group II-A: 1,2-diradyl-sn-glycero-3-phospho-O-tyrosine, 1,2-diradyl-sn-glycero-3-phospho-O-serine, 1,2-diradyl-sn-glycero-3-phospho-O-hydroxyproline and 1,2-diradyl-sn-glycero- 3-phospho-O-threonine;

Group II-B: 1,2-diradyl-sn-glycero-3-diphospho-O-tyrosine, 1,2-diradyl-sn-glycero-3-diphospho-O-serine, 1,2-diradyl-sn-glycero-3-diphospho-O-hydroxyproline and 1,2-diradyl-sn-glycero- 3-diphospho-O-threonine;

Group II-C: 1-O-acyl-sn-glycero-3-phospho-O-tyrosine, 1-O-acyl-sn-glycero-3-phospho-O-serine, 1-O-acyl-sn-glycero-3 -phospho-O-hydroxyproline and 1-O-acyl-sn-glycero-3-phospho-O-threonine; and Group II-D: 1-O-acyl-sn-glycero-3-diphospho-O-tyrosine, 1-O-acyl-sn-glycero-3-diphospho-O-serine, 1-O-acyl-sn-glycero-3 -diphospho-O-hydroxyproline and 1-O-acyl-sn-glycero-3 -diphospho-O-threonine.

Group II-E: 1-O-alkyl-sn-glycero-3-phospho-O-tyrosine, 1-O-alkyl-sn-glycero-3-phospho-O-serine, 1-O-alkyl-sn-glycero-3 -phospho-O-hydroxyproline, and 1-O-alkyl-sn-glycero-3-phospho-O-threonine; and Group II-F: 1-O-alkyl-sn-glycero-3-diphospho-O-tyrosine, 1-O-alkyl-sn-glycero-3-diphospho-O-serine, 1-O-alkyl-sn-glycero-3 -diphospho-O-hydroxyproline, and 1-O-alkyl-sn-glycero-3 -diphospho-O-threonine.

Particularly preferred species of Group II-A are: phosphatidyl-tyrosine, phosphatidyl-serine, phosphatidylthreonine, and phosphatidyl-hydroxyproline.

Particularly preferred species of Group IIB are: tyrosine-O-diphosphate dipalmitoylglycerol, serine-O-diphosphate dipalmitoylglycerol, hydroxyproline-O-diphosphate dipalmitoylglycerol and threonine-O-diphosphate dipalmitoylglycerol;

Particularly preferred species of Group II-E are: 1-O-hexadecyl-sn-glycero-3-phospho-O-tyrosine,1-O-hexadecyl-sn-glycero-3-phospho-O-serine, 1-O-hexadecyl-sn-glycero-3 -phospho-O-hydroxyproline and 1-O-hexadecyl-sn-glycero-3 -phospho-O-threonine; and Particularly preferred species of Group II-F are: 1-O-hexadecyl-sn-glycero-3-diphospho-O-tyrosine, 1-O-hexadecyl-sn-glycero-3-diphospho-O-serine,1-O-hexadecyl-sn-glycero-3-diphospho-O-hydroxyproline and 1-O-hexadecyl-sn-glycero- 3-diphospho-O-threonine.

Spacers

The distance between the lipid linker and the peptide can be adjusted by the insertion of spacer moieties. Spacers suitable for use in the peptide-lipids of the invention have two functional groups capable of binding to functional groups present on the lipid linkers and peptides and serving to conjugate them.

Preferred spacers are:

W: $H_2N$—$(CH_2)_n$—COOH, wherein n=1 to 12, suitable for insertion at the carboxyl terminal of a peptide, connecting it with a lipid linker and those moieties defined below as C.

Y: HOOC—$(CH_2)_n$—COOH, wherein n=1 to 12, suitable for insertion at the amino terminal end of a peptide, to connect it with a phospholipid having an amino functional group. See, for example, in Group III-A below, wherein succinyl is a spacer connecting phosphatidyl-ethanolamine species DPPE and DMPE with N-terminal amino acids of the peptide species.

Z: HO—$(CH_2)_n$—COOH, wherein n=1 to 12, suitable for insertion at the amino terminal end of a peptide, to connect the peptide with a phospholipid having a phosphate terminal group, for example, phosphatidic acid species such as DMPA and DPPA.

Group III: Peptide-lipid conjugates

In order to improve the biological lives of the inhibitors in vivo and to achieve their optimum targeting and release, we have designed the following series of derivatives of protease inhibitory peptides. A number of linkages between phospholipids and peptides are possible. For example, phosphatidic acid can be linked to the amino or the hydroxyl groups of peptides. Alternatively, carboxyl groups of the peptides can be attached to the amino group of a phosphatidyl-ethanolamine.

Yet another strategy for obtaining the peptide phospholipid conjugates is to use suitable linkers, such as those comprising hydroxyamino acids as described previously. A variety of other moieties lend themselves as suitable linkers for conjugating peptides to lipids.

The following peptide-lipid conjugates are described as examples, other therapeutic peptides and enzyme inhibitors similarly can be conveniently derivatized with appropriate lipid moieties by following the procedures provided in the present invention.

Group III-A:

The following are examples of peptide-lipid conjugates wherein the lipid, usually a phospholipid, or species of the lipid linkers described above (X), is attached at the terminal amino group of the peptide.

i-Boc—Tyr—Pro—Ile—Gly—DPPE

DPPA—Ser—Gln—Asn—Tyr—Pro—Ile—Val—NH$_2$

DPPA—Ser—Gln—Asn—Tyr—Acpnt—Ile—Val—NH$_2$

DPPE-Succinyl-Ala—Ala—(D-b-Nal)—Pip—OMe

DPPE-Succinyl-Val—Ser—Gln—Asn—Tyr—Pip—Ile—Val—Gln—NH$_2$

DMPE-Succinyl-Val—Ser—Gln—Asn—Tyr—Pip—Ile—Val—Gln—NH$_2$

-continued

DMPE-Succinyl-Val—Ser—Gln—Asn—Tyr—Diq—Ile—Val—Gln—NH$_2$

DPPE-Succinyl-[D—Phe]—[D-a-Nal]—Pip—[L-a-(OH)—Leu]—Val—NH$_2$

DPPE-Succinyl-Phe(CHOH—CH$_2$N)Phe—Ile—Phe—NH$_2$

DPPE-Succinyl-Phe—O—CH$_2$—CHOH
|
NH$_2$—Phe—O—CH$_2$—CHOH

Boc—Ser(DPP)—Phe—O—CH$_2$—CHOH
|
Boc—Ser—Phe—O—CH$_2$—CHOH

X—Phe(CHOH—CH$_2$N)Phe—Ile—Phe—NH$_2$

X—Phe(CHOH—CH$_2$N)Pro—Ile—Val—NH$_2$

Abbreviations:
Ac=Acetyl; Boc=t-Butyloxycarbonyl; Suc=succinic acid; —OMe=Methyl ester, —NH$_2$=Amide; —NHOH=Hydroxylamide; —NHNH$_2$=Hydrazide; DPPA=1,2 -di-Palmitoyl-phosphatidic acid; DPPE=1,2-di-Palmitoylphosphatidyl ethanolamine; Achx=1-Amino, 1-cyclohexane carboxylic acid; Acpr=1-Amino, 1-cyclopropane carboxylic acid; Acpnt=1-Amino, 1-cyclopentane carboxylic acid; Pip=Pipecolic acid (4-piperidine carboxylic acid); Ava=5-Amino valeric acid, a-(OH)-Leu=L-Leucic acid (2-OH-L-isocaproic acid); Nal=Naphthylalanine; Phe(4-Cl)=p-Chloro phenylalanine; Nva=norvaline; Paa=Phosphonoacetic acid; Chl=Cholic acid. 3,5-di-Aba=3,5-di-Aminobenzoic acid.

X represents phosphatidyl-tyrosine, phosphatidyl-serine, phosphatidyl-threonine, phosphatidyl-hydroxyproline, 1-O-hexadecyl-sn-glycero-3-phospho-O-tyrosine, 1-O-hexadecyl-sn-glycero-3-phospho-O-serine,1-O-hexadecyl-sn-glycero- 3-phospho-O-hydroxyproline, 1-O-hexadecyl-sn-glycero- 3-phospho-O-threonine, 1-O-hexadecyl-sn-glycero- 3-diphospho-O-tyrosine, 1-O-hexadecyl-sn-glycero-3 -diphospho-serine,1-O-hexadecyl-sn-glycero-3-diphosphohydroxyproline, 1-O-hexadecyl-sn-glycero-3-diphosphothreonine, or DPPE-Y or DPPA-Z, wherein Y is HOOC—(CH$_2$)$_n$—COOH;

Z is HO—(CH$_2$)$_n$—COOH; and n=1 to 12.

The linker moieties described here are useful for conjugating lipid groups to a number of therapeutic peptides and protease inhibitors described in, for example, the following publications or patent applications: U.S. Pat. No. 4,743,585; DE 3913272; DE 3840452; DE 3819846; DE 3800233; EP 0 387 231; EP 0 337 714; EP 0 354 522; EP 0 356 223; EP 0 373 576; EP 0 373 549; EP 0 372 537; EP 0 365 992; EP 0 361 341; EP 0 386 611; EP 0 357 332; EP 0 342 541; EP 0 337 714; FR 2646353; WO 9101327; WO 9012804; WO 00399; WO 8910920, WO 8809815. The peptides and the procedures described for the preparation of the said compounds and related intermediates are incorporated herein by reference.

In the examples that follow, X and the abbreviations are as defined above for Group III-A, and C represents H, OH, OMe, NH$_2$, NH—R where R represents C$_{1-12}$ alkyl, benzyl, substituted benzyl, (CH$_2$)$_n$-phenyl where n=1 to 12, 2-methyl pyridyl, phosphatidyl-tyrosine, phosphatidyl-serine, phosphatidyl-threonine, phosphatidyl-hydroxyproline, 1-O-hexadecyl-sn-glycero-3 -phospho-O-tyrosine,1-O-hexadecyl-sn-glycero-3-phosphoserine, 1-O-hexadecyl-sn-glycero-3-phospho-O-hydroxyproline and 1-O-hexadecyl-sn-glycero-3-phospho-O-threonine, 1-O-hexadecyl-sn-glycero-3-diphospho-O-tyrosine, 1-O-hexadecyl-sn-glycero-3-diphospho-O-serine, 1-O-hexadecyl-sn-glycero-3-diphospho-O-hydroxyproline, 1-O-hexadecyl-sn-glycero-3-diphospho-O-threonine, or DPPE-W, wherein W is H$_2$N—(CH$_2$)$_n$—COOH, and n=1 to 12.

Group III-B: Peptide-lipid conjugates based on the peptides of Merck European Patent application # EP 0 337 714 A2

The following are examples of peptide-lipid conjugates wherein the lipid, a species of the lipid linkers described above (X), is attached at the terminal amino group of the peptide or a species (C) is attached at the carboxyl end of the peptide. In preferred species of this class, the peptide is linked to one lipid species, thus X is present only when C is absent or is not a lipid. When C is present, it can be separated from the peptide by the insertion of a W type spacer, described above. When X is present, it can be separated from the peptide by a Y or Z type spacer, also described above.

5(S)-X-Amino-4(S)-hydroxy-6-phenyl-2 (R)-(phenylmethyl)hexanoyl-Leu-Phe-C;

5(S)-X-Amino-4(S)-hydroxy-6-phenyl-2 (R)-(phenylmethyl)hexanoyl-Leu-C;

5(S)-X-amino-4(S)-hydroxy-6-cyclohexyl-2 (R)-(phenylmethyl)hexanoyl-C;

5(S)-X-Amino-4(R)-hydroxy-6-phenyl-2 (R)-(phenylmethyl)hexanoyl-Leu-Phe-C;

5(S)-X-Amino-4(R)-hydroxy-6-phenyl-2 (R)-(phenylmethyl)hexanoyl-Leu-C; and

5(S)-X-amino-4(R)-hydroxy-6-cyclohexyl-2 (R)-(phenylmethyl)hexanoyl-C.

wherein X and C are as defined above.

Group III-C: Peptide-lipid conjugates based on the peptides of Upjohn Publications: SCIENCE, VOL 247 PP 454–456, 1990; and Sawyer, T. K. et al. (1990) in Peptides: Chemistry Structure and Biology (Rivier, J. E. & Garland, G. R. eds.), pp. 855–857

The following are examples of peptide-lipid conjugates of the same type as those presented in Group IIIB.

5(S)-X-Amino-4(S)-hydroxy-6-cyclcohexyl-2(R)-isopropyl-hexanoyl-Ile-C;

5(S)-X-Amino-4(R)-hydroxy-6-cyclcohexyl-2(S)-isopropyl-hexanoyl-Ile-C;

5(S)-X-Amino-4(S)-hydroxy-6-phenyl-2(R)-isopropyl-hexanoyl-Ile-C;

5(S)-X-Amino-4(R)-hydroxy-6-phenyl-2(S)-isopropyl-hexanoyl-Ile-C;

wherein X and C are as defined above.

Group III-D: Peptide-lipid conjugates based on the peptides of the ROCHE European Patent Application #EP 0 346 847 A2

The following are examples of peptide-lipid conjugates of the same type as those presented in Group IIIB.
(3(S)-X-Asparaginyl)-amino-2(R)-hydroxy-4-phenylbutyl-Pro-C;
(3(S)-X-Asparaginyl)-amino-2(S)-hydroxy-4-phenylbutyl-Pro-C;
(3(S)-X-Asparaginyl)-amino-2(R,S)-hydroxy-4-phenylbutyl-Pro-C;
(3(S)-X-Asparaginyl)-amino-2(R,S)-hydroxy-4-phenylbutyl-Pro-Ile-C;
(3(S)-X-Leucyl-Asparaginyl)-amino-2(R,S)-hydroxy-4-phenylbutyl-Pro-Ile-C;
(3(S)-X-Asparaginyl)-amino-2(R)-hydroxy-4-phenylbutyl-N-1,2,3,4-tetrahydro(R,S)isoquinoline carboxyl-C;
(3(S)-X-Asparaginyl)-amino-2(S)-hydroxy-4-phenylbutyl-N-1,2,3,4-tetrahydro(R,S)isoquinoline carboxyl-C;
(3(S)-X-Asparaginyl)-amino-2(R,S)-hydroxy-4-phenylbutyl-N-1,2,3,4-tetrahydro(R,S)isoquinoline carboxyl-C;
(3(S)-X-Asparaginyl)-amino-2(R,S)-hydroxy-4-phenylbutyl-N-decahydro- 3(S)-isoquinoline carboxyl-C;
(3(S)-X-Asparaginyl)-amino-2(R)-hydroxy-4-phenylbutyl-N-decahydro- 3(S)-isoquinoline carboxyl-C; and
(3(S)-X-Asparaginyl)-amino-2(S)-hydroxy-4-phenylbutyl-N-decahydro- 3(S)-isoquinoline carboxyl-C;
wherein X and C are as defined above.

Group III-E: Peptide-lipid conjugates based on the peptides of the SK&F International Patent Application # WO 90/00399; and Publications: NATURE 343:90–92 (1990); PNAS, VOL 86:9752–9756 (1989):

The following are examples of peptide-lipid conjugates of the same type as those presented in Group III-B.
4(S)-(X-Alanyl)amino-3(S)-hydroxy-5-phenyl-pentanoyl-Val-Val-C
4(S)-(X-Alanyl-alanyl)amino-3(S)-hydroxy-5-phenyl-pentanoyl-Val-Val-C
4(S)-(X-Seryl-alanyl-alanyl)amino-3(S)-hydroxy-5-phenyl-pentanoyl-Val-Val-C
4(S)-(X-Alanyl)amino-3(R)-hydroxy-5-phenyl-pentanoyl-Val-Val-C
4(S)-(X-Alanyl-alanyl)amino-3(R)-hydroxy-5-phenyl-pentanoyl-Val-Val-C
4(S)-(X-Seryl-alanyl-alanyl)amino-3(R)-hydroxy-5-phenyl-pentanoyl-Val-Val-C;
wherein X and C are as defined above.

Group III-F: Peptide-lipid conjugates based on the peptides of the HOECHST European Patent # EP 0354 522 A1

The following are examples of peptide-lipid conjugates of the same type as those presented in Group III-B.
X-Val-Phe-Nva-(cyclohexylmethyl(4,4,5,5-tetramethyl-1,3,2 -dioxoborlan-2-yl)methylamide;
X-Val-Phe-Nva-(cyclohexylmethyl,dihydroxyboronyl)methylamide;
X-Val-(L-a-Nal)-Nva-(cyclohexylmethyl(4,4,5,5-tetramethyl-1,3,2-dioxoborlan-2-yl)methylamide;
X-Val-(L-a-Nal)-Nva-(cyclohexylmethyl,dihydroxyboronyl)methylamide;
X-Nva-(cyclohexylmethyl,dihydroxyboronyl)methylamide;
X-Val-(cyclohexylmethyl,dihydroxyboronyl)methylamide;
wherein X is as defined above.

As described in the experimental section, many of the lipid linker species, particularly a phosphatidylhydroxyamino acid, are bifunctional, and can be positioned either at the C-terminal, N-terminal or in the middle at internal sites of the protease inhibitory peptide as desired. That species of lipid linker can also be attached to two sites of the same peptide, using appropriate spacers, if necessary. It is also within the contemplation of the invention to conjugate a monoglyceride or diglyceride directly to a free carboxyl, preferably the terminal carboxyl, of a peptide through the hydroxy group of the lipid.

Peptide Synthesis

Peptides of the invention can be produced by any of the peptide synthesis procedures known to those in the art, for example, solution phase synthesis, fragment condensation, enzyme synthesis, or any of the methods of solid phase synthesis. These peptides can also be produced by recombinant DNA technology. The solution phase method and the solid phase methods are preferred. The solid phase methods are particularly preferred. These methods are well known to those skilled in the art and described in detail in the literature; e.g. Barany, G. and R. B. Merrifield, in *The Peptides*, vol. 2; E. Gross & J. Meienhoffer, eds.; Academic Press, New York, pp 3–284 (1979). Commercially available derivatized amino acids used for the synthesis of peptides described in this invention are: Boc-Ala-OH, Boc-Arg(Tos)-OH, Boc-Asn-OH, Boc-Asp(O-cyclohexyl)-OH, Boc-Asp(OBzl)-OH, Boc-Cys(S- 4-MeBzl)-OH, Boc-Gln-OH, Boc-Glu(O-cyclohexyl)-OH, Boc-Glu(OBzl)-OH, Boc-Gly-OH, Boc-His(Tos)-OH, Boc-His(Bom)-OH, Boc-Ile-OH, Boc-Leu-OH, Boc-Lys(Cl-Z)-OH, Boc-Norleucine, Boc-Norvaline, Boc-Met-OH, Boc-Phe-OH, Boc-Pro-OH, Boc-Ser(Bzl)-OH, Boc-Thr(Bzl)-OH, Boc-Thr(Bzl)-OH, Boc-Trp-OH, Boc-Trp(Formyl)-OH, Boc-Tyr(Br-Z)-OH, and Boc-Val-OH.

Therapeutic applications

Peptides of the invention containing basic amino acids such as lysine, arginine, and histidine may exist in the form of salts such as chloride, acetate, phosphate, citrate, succinate, oxalate, etc. Acetate and hydrochloride salt forms are particularly preferred. Peptides of the invention containing aspartic acid, glutamic acids or phosphate linker moieties may exist in the form of salts such as sodium, potassium, calcium, barium, ammonium or other acceptable cation. For the purposes of this invention, peptides of the invention and their acid addition salts are considered to be one and the same.

The peptides and peptide-lipid conjugates of the present invention are useful as inhibitors of viral proteases and therefore could be used as therapeutic agents for example for the prevention or treatment of infection by human immunodeficiency virus (HIV), and subsequent disease conditions such as acquired immunodeficiency syndrome (AIDS) and AIDS related complex (ARC).

The peptide lipid conjugates are also useful in improving the efficacy of other protease inhibitors, such as inhibitors of renin. Renin is a protease of approximately 40,000 MW secreted in the kidney by juxtaglomerular cells surrounding the afferent arterioles of the cortical glomeruli. Renin itself has no activity, but acts on a protein substrate, angiotensinogen, to split off the inactive decapeptide, angiotensin I, which is then converted through the splitting off of two C-terminal peptides, to the active pressor agent, the octapeptide angiotensin-II. Angiotensin-II is the most potent pressor made in the body and it exerts this pressor action by a direct effect on arteriolar smooth muscle. Secretion of renin is stimulated in various disorders and causes hypertension. An approach to the therapy of hypertension comprises the administration of renin inhibitory peptides which are renin substrate analogues, a strategy comparable to the administration of HIV protease inhibitors in the therapy of HIV infection. Lipid conjugates of renin inhibitory peptides, having the composition of the peptide-lipids of the invention, can similarly contribute to the effective therapy of hypertension by providing renin peptides in a form that resists clearance and degradation and promotes efficient uptake by the cells.

The present invention also relates to the use of the therapeutic peptides and peptide conjugates of the invention and their physiologically acceptable salts for the preparation of pharmaceutical formulations which can be employed as medicaments in human and veterinary medicine. For this purpose, it is possible to convert them into a suitable form for administration together with at least one vehicle or auxiliary. Suitable vehicles are organic and inorganic substances which are suitable for enteral (for example, oral), parenteral, topical, transdermal or nasal administration and which do not react with the active drug substances. The indicated formulations can be sterilized and/or contain auxiliaries, such as lubricants, preservatives stabilizers, wetting agents, emulsifiers, buffers, colorings and flavoring.

The active peptides may be administered parenterally, that is by subcutaneous, intramuscular, intraperitoneal, or intravenous injection. The pharmaceutical formulations suitable for injectable use include aqueous solutions or dispersions and powders for the extemporaneous preparation of injectable solutions or dispersions. It is possible also to freeze-dry the peptides and to use the lyophilizates obtained, for example, for the preparation of products for injection. In all cases, the form must be sterile and the solution must be fluid to the extent that easy syringability exists. It must be stable under the conditions of manufacture and storage and must be preserved against contaminations of microorganisms, such as for example, bacteria and fungi. The carrier can be a solvent or a dispersion medium containing, for example, water, or a polyol such as glycerol, and suitable mixtures thereof. Compositions for intramuscular use may also contain minor amounts of salts, acids, and bases to adjust tonicity and buffer the solution. Suitable buffering and isotonicity agents are readily determinable by persons skilled in the art.

Oral or nasal administration is also possible especially with peptide-lipid conjugates. Formulations for oral ingestion are in the form of tablets, capsules, pills, ampoules of powdered active agent, or oily or aqueous suspensions or solutions. Tablets or other non-liquid oral compositions may contain acceptable excipients, known to the art for the manufacture of pharmaceutical compositions, comprising diluents, such as lactose or calcium carbonate; binding agents such as gelatin or starch; and one or more agents selected from the group consisting of sweetening agents, flavoring agents, coloring or preserving agents to provide a palatable preparation. Moreover, such oral preparations may be coated by known techniques to further delay disintegration and absorption in the intestinal tract. Such oral compositions and preparations should contain at least 0.1% of active peptide, although the percentages of the compositions may vary widely. The amount of therapeutically active compound in such compositions is such that a suitable dosage will be obtained in a convenient volume for ingestion.

Formulations for nasal administration may be in the form of liquids and optionally may contain absorption promoting substances, for example, a lactone of a water-soluble organic acid, and other compounds of similar function well known to those trained in the art. The nasal formulations may also be in the form of an aerosol comprising the peptide together with an extender which may be an amino acid, for example, methionine.

Transdermal application formulations can comprise the peptides and their lipid conjugates, optionally incorporated into a suitable topical carrier, or a dermal patch. The compounds can be combined with a penetration-enhancing agent, for example, dimethylsulfoxide (DMSO), dimethylformamide, dimethylacetamide, or Azone®, azacycloheptane-2-one. Both topical carriers and the use of penetration enhancers are disclosed by Blaug, S., Chap. 87 *Remington's Pharmaceutical Sciences*, 15th Ed. Mack Publishing Co., Easton, Pa. 18042 (1975).

In the therapy of HIV-infected patients, the lipid conjugated protease inhibiting peptide will be administered parenterally, orally, or nasally. Parenteral doses are usually from 0.01 to 1 gm every 3–8 hours. Nasal or oral doses may be from 2 to 10 times the parenteral dose, depending on bioavailability of the peptide, and its retention in the plasma and tissues. The most efficacious dose can be readily determined by standard pharmacokinetic and toxicological studies in animals and humans.

EXPERIMENTAL PROCEDURES

The amino acid abbreviations used are those commonly employed in the peptide art and described in the literature, eg. IUPAC-IUB Commission on Biochemical Nomenclature, *J. Biol. Chem.* 247, 979–982 (1972). Additional abbreviations used are: Ac=Acetyl; Boc=t-Butyloxycarbonyl; Suc-succinic acid; —OMe=Methyl ester, —NH$_2$=Amide; —NHOH=Hydroxylamide; —NHNH$_2$=Hydrazide; DPPA=1,2-dipalmitoylphosphatidic acid; DPPE=1,2-dipalmitoylphosphatidyl ethanolamine; Achx=1-Amino, 1-cyclohexane carboxylic acid; Acpr=1-Amino, 1-cyclopropane carboxylic acid; Acpnt=1-Amino, 1-cyclopentane carboxylic acid; Pip=Pipecolic acid (4-piperidine carboxylic acid); Ava=5-Amino valerie acid, a-(OH)-Leu=L-Leucic acid (2-OH-L-isocaproic acid); Nal=Naphthylalanine; Phe(4-Cl)=p-Chloro phenylalanine; Nva=norvaline; Paa=Phosphonoacetic acid; Chl=Cholic acid. 3,5-di-Aba=3,5-diaminobenzoic acid. Amino acids discussed herein are of the L-form unless otherwise mentioned.

All the temperatures described are in degree Celsius and are uncorrected. Evaporations were carried out under vacuum below 35° C. TLC was carried out using E.Merck precoated plates and the spots were visualized by exposure to UV light, iodine, ninhydrin spray, phosphorous spray, or sulfuric acid spray followed by charring as appropriate. Analytical HPLC was carried out using a Beckman system and Vydac reverse phase columns (C-4 or C-18 as appropriate). Preparative HPLC was carried out using a Waters Deltaprep system using either reverse phase or silica columns. Purity and authenticity of the compounds were established by TLC, analytical HPLC, amino acid analysis, elemental analysis, UV spectra, NMR, FAB-MS as required and appropriate.

The chemical reactions described below are generally disclosed in terms of their general application to the preparation of peptides of the invention. Occasionally, the reaction may not be applicable as described to each peptide included within the disclosed scope. The peptides for which this occurs will be readily recognized by those skilled in the art. In all such cases, either the reactions can be successfully performed by conventional modifications known to those skilled in the art, e.g. by appropriate protection of interfering groups, by changing to alternative conventional reagents, or by routine modification of reaction conditions. Alternatively, other reactions disclosed herein or otherwise conventional will be applicable to the preparation of the corresponding peptides of the invention. In all preparative methods, all starting materials are known or readily preparable from known starting materials.

Without further elaboration, it is believed that one skilled in the art can, using the preceding description, utilize the invention to its fullest extent. The following preferred embodiments are, therefore, to be construed as merely illustrative and not limitative of the remainder of the disclosure in any way whatsoever. In the following examples, all temperatures are set forth uncorrected in degrees Celsius; unless otherwise indicated, all parts and percentages are by weight.

The present invention is described below in detail using the following examples, but the methods described below are applicable for the preparation of all peptides covered by the scope of the invention and are not limited to the Examples given below.

EXAMPLE 1

General procedure for coupling phosphatidic acid to the amino group of a peptide 1,2-Dipalmitoyl-sn-glycero-3-phosphatidic acid.2Na (DPPA.2Na; Avanti Polar Lipids, Birmingham Ala.; MW: 697.84; 698 mg, 1 mmol) was partitioned between chloroform:methanol (2:1 (v/v); 200 ml) and cold 1N HCl (50 ml). The aqueous layer was re-extracted with chloroform methanol (2:1 (v/v); 100 ml). The combined organic phase was evaporated and dried under vacuum over $P_2O_5$. The resulting free phosphatidic acid was dissolved in a mixture of DMF (2 ml) and pyridine (2 ml) and to the solution were added the appropriate peptide having a free amino group (1 mmol) followed by N,N'-dicyclohexylcarbodiimide (DCC; Aldrich Chemical Co. Milwaukee, Wis., MW: 206, 620 mg, 3 mmol). The reaction mixture was stirred for 24 hours at room temperature. The solvents were evaporated and the product was purified by flash chromatography over silica gel column (2.5×50 cm) using a linear gradient of 0 to 50% methanol in chloroform. Fractions containing the desired product as indicated by TLC and HPLC were pooled and evaporated. The product was further purified, if necessary, by preparative HPLC or by crystallization.

EXAMPLE 1A

A: DPPA-Ser-Gln-Asn-Tyr-Pro-Ile-Val-NH$_2$ and

EXAMPLE 1B

DPPA-Ser-Gln-Asn-Tyr-Acpnt-Ile-Val-NH$_2$ peptides were prepared by the above procedure.

EXAMPLE 2

General procedure for coupling phosphatidic acid to the hydroxy group of a peptide 1,2-Dipalmitoyl-sn-glycero-3-phosphatidic acid (1 mmol) prepared as above was dissolved in a mixture of DMF (2 ml) and pyridine (2 ml) and to the solution were added the appropriate peptide having a free hydroxyl group (1 mmol) followed by DCC (620 mg, 3 mmol). The reaction was carried out and the product was isolated as described in Example 1.

The condensation of the phosphatidic acid and the hydroxyl group of a peptide was also conveniently carried out by using 2,4,6-triisopropylbenzenesulfonyl chloride (TPS-Cl; Aldrich Chemical Co., Milwaukee, Wis.; MW: 302.86; 758 mg, 2.5 mmol) as a coupling agent in place of DCC.

EXAMPLE 3

General procedure for coupling a peptide containing a free carboxyl group to the amino group of a phosphatidylethanolamine A mixture of the appropriate peptide (1 mmol), phosphatidyl-ethanolamine (1 mmol) were dissolved in pyridine (5 ml) and DCC (3 mmol) followed by 1-hydroxybenzotriazole (HOBt; Aldrich Chemical Co., HOBt, MW: 153; 450 mg, 3 mmol) were added. The reaction mixture was stirred for 24 hours at room temperature and the product was purified by silica gel chromatography as described in Example 1.

EXAMPLE 3A i-Boc-Tyr-Pro-Ile-Gly-DPPE was prepared by the above procedure.

EXAMPLE 4

General procedure for coupling peptide containing a free carboxyl group to the hydroxy group of a diacyl or dialkyl glycerol A mixture of the appropriate peptide (1 mmol), diacyl or dialkyl glycerol (1 mmol) were dissolved in pyridine (5 ml) and DCC (3 mmol) followed by 4-dimethylaminopyridine (Aldrich Chemical Co., DMAP, MW: 122.17; 122 mg, 1 mmol) were added. The reaction mixture was stirred for 24 hours at room temperature and the product was purified by silica gel chromatography as described in Example 1.

EXAMPLE 5

Preparation of N-tert.Butyloxycarbonyl-Serine-Hydroxysuccinimide Ester (Boc-Ser-OSu) MW: 302.26

Boc-Ser-OH (20.52 g, 100 mmol) and N-hydroxysuccinimide (Aldrich Chemical Co., Milwaukee, Wis.; MW: 115.09; 23.3 g, 200 mmol) were dissolved in dry THF (400 ml). The solution was cooled to −10° C., DCC (MW: 206.33; 30.10 g; 150 mmol) was added. The mixture was stirred for 2 hours at −10° C. and overnight at room temperature. The solvents were evaporated under vacuum, and the residue was stirred in ethyl acetate (1 l) and filtered to remove insoluble material. The resulting filtrate was washed successively with water (3×250 ml), cold 1N HCl (3×250 ml), water (3×250 ml), cold 10% NaHCO$_3$ (3×250 ml) and water (3×250 ml) and dried over anhydrous sodium sulfate. After evaporation the residue was crystallized from isopropyl alcohol.

Boc-Tyr-OSu, Boc-Hyp-OSu and Boc-Thr-OSu were prepared similarly.

EXAMPLE 6

Preparation of 1,2-Dipalmitoyl-sn-glycero-3-phospho-O-(N-Boc)-Ser-OSu; Boc-Ser(ODPP)-OSu: MW: 850.17

1,2-Dipalmitoyl-sn-glycero-3-phosphatidic acid (1 mmol) was dissolved in anhydrous pyridine (5 ml) and 2,4,6-triisopropylbenzenesulfonyl chloride (TPS-Cl, 758 mg, 2.5 mmol) followed by Boc-Ser-OSu (MW: 302.26; 302 mg, 1 mmol) was added. The reaction mixture was stirred under dry nitrogen atmosphere for 16 hours at room temperature. The reaction was then quenched by adding water (1 ml) and the solvents were evaporated under vacuum. The residue was dissolved in chloroform (5 ml) and loaded onto a silica gel 60 column (2.5 cm×45 cm) equilibrated with chloroform. The column was eluted with a gradient of chloroform (500 ml) to 15% MeOH in chloroform (500 ml). Fractions containing the desired product (as indicated by TLC) were pooled and evaporated to furnish Boc-Ser(ODPP)-OSu.

Boc-Tyr(ODPP)-OSu, Boc-Hyp(ODPP)-OSu and Boc-Thr(ODPP)-OSu were prepared similarly.

EXAMPLE 7

General procedure for coupling phosphatidyl-serine, to a peptide containing a free amine function.

Boc-Ser(ODPP)-OSu (0.1 mmol) and the peptide in question containing a free amine function (0.1 mmol) were dissolved in DMF (2 ml) and pyridine (2 ml) and stirred for 24 hours at room temperature. The solvents were evaporated and the product was purified by flash chromatography over silica gel column (2.5×50 cm) using a linear gradient of 0 to 50% methanol in chloroform. Fractions containing the desired product as indicated by TLC and HPLC were pooled and evaporated. The product was further purified, if necessary, by preparative HPLC or by crystallization and deprotected by treatment with trifluoroacetic acid (2 ml) for 12 hours at room temperature. The acid was removed by evaporation under vacuum and the product was isolated by lyophilization from water.

Peptides linked to phosphatidyl-tyrosine, phosphatidyl-hydroxyproline and phosphatidyl-threonine were prepared similarly.

EXAMPLE 7A

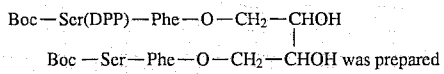

Boc—Ser—Phe—O—CH$_2$—CHOH was prepared according to the above procedure.

EXAMPLE 8

Preparation of 1,2-Dipalmitoyl-sn-glycero-3-phospho-O-(N-Fmoc)-Ser-OBzl (Fmoc-Ser(ODPP)-OBzl)

Starting from Fmoc-Ser-OBzl the title compound was prepared following the procedure described for Boc-Ser(ODPP)-OSu.

Fmoc-Tyr (ODPP)-OBzl, Fmoc-Hyp(ODPP)-OBzl and Fmoc-Thr(ODPP)OBzl were prepared similarly.

EXAMPLE 9

General procedure for coupling a peptide containing a free carboxyl group to phosphatidyl-serine Fmoc-Ser(ODPP)-OBzl (0.1 mmol) was dissolved in DMF (2 ml) and piperidine (0.2 ml) and the mixture was stirred under dry nitrogen atmosphere for 4 hours and the solvents were evaporated under vacuum. The residue was dissolved in a dry DMF (5 ml) and the peptide in question containing a free carboxyl group (0.1 mmol) was added to it followed by DCC (0.1 mmol) and HOBt (0.1 mmol). The reaction mixture was stirred for 24 hours at room temperature. The solvents were evaporated and the product was purified by flash chromatography over silica gel column (2.5×50 cm) using a linear gradient of 0 to 50% methanol in chloroform. Fractions containing the desired product as indicated by TLC and HPLC were pooled and evaporated. The product was further purified, if necessary, by preparative HPLC or by crystallization. The product was then dissolved in DMF (5 ml) and hydrogenated in the presence of palladium-carbon (5%) catalyst (200 mg). The catalyst was removed by filtration and the product was purified by silica gel chromatography as described above.

Peptides containing phosphatidyl-tyrosine, phosphatidyl-hydroxyproline and phosphatidyl-threonine were prepared similarly.

EXAMPLE 10

Preparation of Boc-Serine(O-diphosphate-dipalmitoylglycerol)-N-hydroxysuccinimide ester (Boc-Ser(O-DP-DPG)-ONSu)

A. Boc-Serine(O-phosphate)-N-hydroxysuccinimide ester

Boc-Ser-OSu (MW: 302.26; 302 mg, 1 mmol) was dissolved in triethyl phosphate (5 ml) and cooled to −5° C. POCl$_3$ (MW 153.33; 460 mg, 3 mmol) was added to the above solution and the reaction mixture was stirred under dry nitrogen atmosphere for 16 hours at −10° C. Ether (20 ml) was added and the resulting precipitate was separated from the supernatant by decantation and the residue was washed with ether (20 ml each). The residue was resuspended in ice cold water (10 ml) and the pH was immediately adjusted to 7.5 by adding 1N NaOH. The solution was stirred for 1 hour at 0° C. while maintaining the pH at 7.5 and lyophilized. The resulting product was dissolved in water (5 ml) and loaded onto a DEAE Sephadex A-25 column (1 cm×10 cm) equilibrated with 0.01M ammonium bicarbonate (pH 7). The column was eluted with a gradient of 0.01M ammonium bicarbonate to 0.3M ammonium bicarbonate (pH 7). Fractions containing the desired product (as indicated by TLC) were pooled and lyophilized to furnish Boc-Ser(O-phosphate)-Osu.

B. 1,2-Dipalmitoyl-sn-glycero-3-phosphoromorpholidate (DPPA-Morpholidate)

1,2-Dipalmitoyl-sn-glycero-3-phosphatidic acid (DPPA, 650 mg, 1 mmol) and morpholine (350 mg, 4 mmol) were dissolved in chloroform (10 ml), t-butanol (10 ml) and water (1 ml). The solution was stirred under gentle reflux for 2 hours while adding a solution of DCC (825 mg, 4 mmol) in t-butanol (10 ml). The mixture was stirred for an additional 4 hours and evaporated to dryness and suspended in water (100 ml) and was extracted three times with ether (100 ml), evaporated to dryness and lyophilized.

C. Coupling of DPPA-Morpholidate and Boc-Ser(O-phosphate)-OSu

DPPA-Morpholidate (0.5 mmol) and Boc-Ser(O-phosphate)-OSu (0.3 mmol) were dissolved in anhydrous pyridine (25 ml). The solution was evaporated to dryness in vacuo five times from anhydrous pyridine, followed by the addition of anhydrous pyridine (5 ml). The reaction mixture was stirred at 40° C. and evaporated to dryness. The product was dissolved in chloroform:methanol:water (2:3:1) and loaded onto a DEAE Sephadex A-25 column (1 cm×10 cm) equilibrated with chloroform:methanol:water (2:3:1). The column was eluted with a linear gradient of 0 to 0.3M ammonium bicarbonate in the same solvent. Fractions containing the desired product (as indicated by TLC) were pooled, concentrated to a 60 ml volume and extracted 5 times with chloroform (50 ml each). The cloroform solution was evaporated to furnish Boc-Serine(O-diphosphate dipalmitoylglycerol)-N-hydroxysuccinimide ester.

Boc-Tyr(O-DP-DPG)-ONSu, Boc-Hyp(O-DP-DPG)-ONSu and Boc-Thr(O-DP-DPG)-ONSu were prepared similarly.

EXAMPLE 11

General procedure for coupling Serine-O-diphosphate dipalmitoylglycerol to a peptide containing a free amine function.

Boc-Ser(O-DP-DPG)-ONSu (0.1 mmol) and the peptide in question containing a free amine function (0.1 mmol) were dissolved in DMF (2 ml) and pyridine (2 ml) and stirred for 24 hours at room temperature. The solvents were evaporated and the product was purified by flash chromatography over silica gel column (2.5×50 cm) using a linear gradient of 0 to 50% methanol in chloroform. Fractions containing the desired product as indicated by TLC and HPLC were pooled and evaporated. The product was further purified, if necessary, by preparative HPLC or by crystallization and deprotected by treatment with trifluoroacetic acid (2 ml) for 12 hours at room temperature. The acid was removed by evaporation under vacuum and the product was isolated by lyophilization from water.

Tyrosine-O-diphosphate dipalmitoylglycerol, hydroxyproline-O-diphosphate dipalmitoylglycerol and threonine-O-diphosphate dipalmitoylglycerol containing peptides were prepared similarly.

EXAMPLE 12

Fmoc-Serine(O-diphosphate dipalmitoylglycerol)-Benzyl Ester (Fmoc-Ser(O-DP-DPG)-OBzl)

Starting from Fmoc-Ser-OBzl and DPPA-Morpholidate the title compound was prepared following the procedure described in Example 11.

Fmoc-Tyr(O-DP-DPG)-OBzl, Fmoc-Hyp(O-DP-DPG)-OBzl and Fmoc-Thr(O-DP-DPG)-OBzl were prepared similarly.

EXAMPLE 13

General procedure for coupling a peptide containing a free carboxyl group to Serine-O-diphosphate dipalmitoylglycerol Starting from Fmoc-Ser(O-DP-DPG)-OBzl, the title compound was prepared by deprotection of the Fmoc- group, followed by the coupling reaction, the catalytic hydrogenation reaction and the purification procedure described above.

Corresponding tyrosine-O-diphosphate dipalmitoylglycerol, hydroxyproline-O-diphosphate dipalmitoylglycerol and threonine-O-diphosphate dipalmitoylglycerol containing peptides were prepared similarly.

EXAMPLE 14

Preparation of 1-O-hexadecyl-sn-glycero-3-phospho-O-(N-Boc)-Ser-OSu

Boc-Ser(O-phosphate)-OSu (1 mmol) was dissolved in anhydrous pyridine (5 ml) and 2,4,6-triisopropylbenzenesulfonyl chloride (TPS-Cl; Aldrich Chemical Co., Milwaukee, Wis.; MW: 302.86; 758 mg, 2.5 mmol) was added followed by 1-O-Hexadecyl-sn-glycerol. The reaction mixture was stirred under dry nitrogen atmosphere for 16 hours at room temperature. The reaction was then quenched by adding water (1 ml) and the solvents were evaporated under vacuum. The residue was dissolved in chloroform (5 ml) and loaded onto a silica gel 60 column (2.5 cm×45 cm) equilibrated with chloroform. The column was eluted with a gradient of chloroform (500 ml) to 15% MeOH in chloroform (500 ml). Fractions containing the desired product (as indicated by TLC) were pooled and evaporated to furnish the title compound.

Preparation of 1-O-hexadecyl-sn-glycero-3-phospho-O-(N-Boc)-Tyr-Osu, 1-O-hexadecyl-sn-glycero-3-phospho-O-(N-Boc)-Hyp-OSu and 1-O-hexadecyl-sn-glycero-3-phospho-O-(N-Boc)-Thr-OSu were carried out in a similar manner.

EXAMPLE 15

General procedure for coupling 1-O-hexadecyl-sn-glycero-3-phospho-serine to a peptide containing free amine function This coupling reaction, subsequent deprotection and purification of the product was carried out following the procedure described in Example 9 except for using 1-O-hexadecyl-sn-glycero-3-phospho-O-(N-Boc)-Ser-OSu in place of Boc-Ser(ODPP)-OSu.

Peptides containing 1-O-hexadecyl-sn-glycero-3-phospho-O-tyrosine, 1-O-hexadecyl-sn-glycero-3-phospho-O-hydroxyproline and 1-O-hexadecyl-sn-glycero-3-phospho-O-threonine were prepared in a similar manner.

EXAMPLE 16

Preparation of 1-O-hexadecyl-sn-glycero-3-phospho-O-(Fmoc)-Ser-OBzl

Starting from Fmoc-Ser-OBzl the title compound was prepared following the procedure described for the preparation of 1-O-hexadecyl-sn-glycero-3-phospho-O-(N-Boc)-Ser-OSu.

Preparation of 1-O-hexadecyl-sn-glycero-3-phospho-O-(Fmoc)-Tyr-OBzl, 1-O-hexadecyl-sn-glycero-3-phospho-O-(Fmoc)-Hyp-OBzl and 1-O-hexadecyl-sn-glycero-3-phospho-O-(Fmoc)-Thr-OBzl were carried out similarly.

EXAMPLE 17

General procedure for coupling a peptide containing free carboxyl group to 1-O-hexadecyl-sn-glycero-3-phospho-serine Starting from 1-O-hexadecyl-sn-glycero-3-phospho-O-(Fmoc)-Ser-OBzl, deprotection of the Fmoc- group, the coupling reaction, catalytic hydrogenation followed by purification as described in Example 10.

Peptides containing 1-O-hexadecyl-sn-glycero-3-phosphotyrosine, 1-O-hexadecyl-sn-glycero-3-phospho-hydroxyproline and 1-O-hexadecyl-sn-glycero-3-phospho-threonine were prepared in a similar manner.

EXAMPLE 18

Preparation of 1-O-hexadecyl-sn-glycero-3-diphospho-O-(N-Boc)-Ser-OSu

Boc-Ser(O-phosphate)-OSu (1 mmol) was converted to the corresponding morpholidate by reacting with DCC and morpholine. The product was then reacted with 1-O-hexadecylglycerol- 3-phosphate as described for the preparation of Boc-Ser(O-DP-DPG)-OSu.

Preparation of 1-O-hexadecyl-sn-glycero-3-diphospho-O-(N-Boc)-Tyr-OSu, 1-O-hexadecyl-sn-glycero-3-diphospho-O-(N-Boc)-Hyp-OSu and 1-O-hexadecyl-sn-glycero-3-diphospho-O-(N-Boc)-Thr-OSu were carried out in a similar manner.

EXAMPLE 19

General procedure for coupling 1-O-hexadecyl-sn-glycero-3-diphospho-serine to a peptide containing free amine function This coupling reaction, subsequent deprotection and purification of the product was carried out following the procedure described in Example 9 except for using 1-O-hexadecyl-sn-glycero-3-diphospho-O-(N-Boc)-Ser-OSu in place of Boc-Ser(O-DP-DPG)-OSu.

Peptides containing 1-O-hexadecyl-sn-glycero-3-diphospho-O-tyrosine, 1-O-hexadecyl-sn-glycero-3-diphospho-O-hydroxyproline and 1-O-hexadecyl-sn-glycero-3-diphospho-O-threonine were prepared in a similar manner.

EXAMPLE 20

Preparation of 1-O-hexadecyl-sn-glycero-3-diphospho-O-(Fmoc)-Ser-OBzl

Starting from Fmoc-Ser-OBzl the title compound was prepared following the procedure described for the preparation of 1-O-hexadecyl-sn-glycero-3-diphospho-O-(N-Boc)-Ser-OSu.

Preparation of 1-O-hexadecyl-sn-glycero-3-diphospho-O-(Fmoc)-Tyr-OBzl, 1-O-hexadecyl-sn-glycero-3-diphospho-O-(Fmoc)-Hyp-OBzl and 1-O-hexadecyl-sn-glycero-3-diphospho-O-(Fmoc)-Thr-OBzl were carried out in a similar manner.

EXAMPLE 21

General procedure for coupling a peptide containing free carboxyl group to 1-O-hexadecyl-sn-glycero-3-diphospho-serine Starting from 1-O-hexadecyl-sn-glycero-3-diphospho-O-(Fmoc)-Ser-OBzl, the title compound was obtained by deprotection of the Fmoc- group, followed by the coupling reaction, the catalytic hydrogenation and the purification procedure described in Example 9.

Peptides containing 1-O-hexadecyl-sn-glycero-3-diphospho-O-tyrosine, 1-O-hexadecyl-sn-glycero-3-diphospho-O-hydroxyproline and 1-O-hexadecyl-sn-glycero-3-diphospho-O-threonine were prepared in a similar manner.

EXAMPLE 22

Preparation of 1,2-Dipalmitoyl-sn-glycero-3-phospho-O-(N-Succinyl)-ethanolamine DPPE-Succinic Acid MW: 791.03

To a solution of 1,2-Dipalmitoyl-sn-glycero-3-phosphatidyl ethanolamine (DPPE; Avanti Polar Lipids, Birmingham, Ala.; MW: 690.96; 346 mg, 0.5 mmol) in chloroform (10 ml), succinic anhydride (Sigma Chemical Co., St. Louis, Mo.; MW: 100.7, 100 mg, 1 mmol) dissolved in chloroform (10 ml) and triethylamine (0.1 ml) were added. The reaction mixture was stirred under dry nitrogen atmosphere for 16 hours at room temperature. The reaction was monitored by running TLC at various intervals. After the reaction is completed, the solvents were evaporated under vacuum and the residue was dissolved in chloroform (5 ml) and loaded onto a silica gel 60 column (2.5 cm×45 cm) equilibrated with chloroform. The column was eluted with a gradient of chloroform (500 ml) to 15% MeOH in chloroform (500 ml). Fractions containing the desired product (as indicated by TLC) were pooled and evaporated to furnish DPPE-Succinic Acid ACID.

Preparation of 1,2-Dimyristoyl-sn-glycero-3-phospho-O-(N-Succinyl)-ethanolamine, DMPE-SUCCINIC ACID, was carried out similarly.

EXAMPLE 23

Preparation of

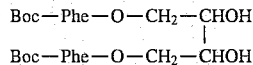

A mixture of Boc-Phe-OH (5.3 g, 20 mmol), triethylamine (TEA; MW: 101.19; 3.1 g, 31 mmol), anhydrous KF (1.2 g, 20 mmol) and 1,3-dibromobutane-2,3-diol (Br-CH$_2$—CHOH—CHOH-CH$_2$—Br, 2.5 g, 10 mmol) was dissolved in DMF (25 ml) and the solution was stirred for 24 hr at 45° C. The solvent was evaporated under vacuum and residue was dissolved in EtAc (330 ml), extracted with 10% sodium bicarbonate (3×50 ml), water (3×50 ml), 10% citric acid (3×50 ml) and water (3×50 ml). The organic phase was dried over anhydrous sodium sulphate and evaporated under vacuum and the residue was crystallized from acetonitrile to furnish the product as white amorphous powder.

EXAMPLE 24

Preparation of

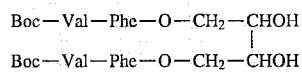

The compound from example 23 (616 mg, 1 mmol) was dissolved in anhydrous TFA (5 ml) and stirred for 15 minutes. The solvent was evaporated and the residue triturated with ether and filtered. The product was dissolved in DMF (20 ml) and cooled to −10° C. Boc-Val-OH (MW: 217.14, 696 mg, 3 mmol), HOBt (456 mg, 3 mmol) and DCC (620 mg, 3 mmol) were added to the above solution. The reaction mixture was stirred for 2 hours at −10° C. and for 16 hours at room temperature. The solvents were then evaporated under vacuum, and the residue was dissolved in ethyl acetate (250 ml) and filtered to remove insoluble material. The resulting filtrate was washed successively with water (3×50 ml), cold 1N HCl (3×50 ml), water (3×50 ml), cold 10% NaHCO$_3$ (3×50 ml) and water (3×50 ml) and dried over anhydrous sodium sulfate. Evaporation of the solvent provided the crude product which was purified by crystallization from acetonitrile.

EXAMPLE 25

Preparation of

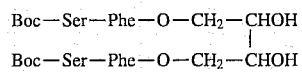

The title compound was prepared following the procedure described for Example 24 except using Boc-Ser-OH instead of Boc-Val-OH.

EXAMPLE 26

Preparation of

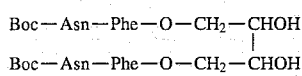

The title compound was prepared following the procedure described for Example 24 except using Boc-Asn-OH instead of Boc-Val-OH.

EXAMPLE 27

General method for the synthesis of peptides by the solid phase method.

A. Resin Peptide Synthesis

Boc-amino acyl-benzyl ester resin or Boc-amino acyl-(4-methyl)benzhydrylamine resin (Boc-AA-Resin, 2 g, 1 mmol) placed in a reaction vessel of Beckman 990 B Peptide Synthesizer (Beckman Instruments, Palo Alto, Calif.) and subjected to the following operations. Each step is carried out one time unless specified otherwise, and reagents and solvents after each step are separated from the peptide resin by filtration under nitrogen.

| Step | Reagent/solvent/No of times | Mix Time (minutes) |
|---|---|---|
| 1 | DCM (30 ml, 3 times) | 1.5 |
| 2 | TFA-DCM (1:1) (30 ml) | 1.5 |
| 3 | TFA-DCM (1:1) (30 ml) | 30.0 |
| 4 | DCM (30 ml, 3 times) | 1.5 |
| 5 | Methanol (30 ml, 3 times) | 1.5 |
| 6 | DCM (30 ml, 3 times) | 1.5 |
| 7 | TFA-DCM (1:1) (30 ml) | 1.5 |
| 8 | TFA-DCM (1:1) (30 ml) | 5.0 |
| 9 | DCM (30 ml, 3 times) | 1.5 |
| 10 | DMF (30 ml, 3 times) | 1.5 |
| 11 | Boc—Thr(Bzl)—OH/HOBt/DCC (4 mmol each) in DMF (20 ml) | 240.0* |
| 12 | DCM (30 ml, 3 times) | 1.5 |
| 13 | Methanol (30 ml, 3 times) | 1.5 |
| 14 | DCM (30 ml, 3 times) | 1.5 |

*Coupling reaction was carried out for an average of 4 hours, as in this case, or until a ninhydrin test (Kaiser E. T. et al, Anal. Biochem. 34, 595–8, 1969) showed a negative result indicating the absence of free amino groups. The same sequence of reactions was repeated using appropriate amino acid derivatives until the required peptide chain was assembled on the resin. After completion of the synthesis, the resin was removed from the vessel and dried under vacuum.

B. Cleavage of the Resin-Peptide using Hydrogen Fluoride (HF):

Peptides containing free carboxyl groups or carboxamide function at the C-terminal are prepared by treating the corresponding benzyl ester linked or 4-methylbenzhydrylamine linked peptide resins according to the following procedure. The dried peptide resin (1 g), anisole (1 ml) and p-cresol (0.1 g) were placed in a Kel F reaction vessel. The vessel was placed in a bath of liquid nitrogen and anhydrous HF (15 ml) was condensed into the vessel. The reaction mixture was stirred at −10° C. for 1 hour and HF was removed by evaporation under vacuum. The residue was triturated with dry ether (50 ml), filtered and washed with additional quantity of ether (3×50 ml). Peptide product in the mixture was isolated by extracting with glacial acetic acid (3×50 ml) followed by lyophilization of the solvent.

C. Preparation of peptide methyl esters by transesterification:

Boc-peptidyl-benzyl ester resin (1 g) was stirred with methanol (10 ml) and triethylamine (1 ml) for 18 hours at room temperature. The resin was filtered and washed three times with methanol (20 ml each time) and the combined filtrate was evaporated to provide peptide methyl esters. Some of the peptides prepared by this method contain protecting groups for other functional groups which are very conveniently deprotected by treatment with liquid HF as described above. The resulting products were purified as described below.

D. Preparation of peptide hydrazides:

Boc-peptidyl-benzyl ester resin (1 g) was stirred with methanol (10 ml) and anhydrous hydrazine (1 ml) for 18 hours at room temperature. The resin was filtered and washed three times with methanol (20 ml each time) and the combined filtrate was evaporated to provide peptide hydrazides esters. Some of the peptides prepared by this method contain protecting groups for other functional groups which are very conveniently deprotected by treatment with liquid HF as described above. The resulting products were purified as described below.

E. Peptide Purification:

Peptide powder obtained above (200 mg) was dissolved in 1N acetic acid (3 ml), loaded to a Sephadex G-25 (superfine) column (1.5 cm×100 cm) and eluted with 1N acetic acid. The eluent fractions containing the peptide were pooled and freeze dried. The resulting peptide (50 mg) was further purified by preparative reverse phase high performance chromatography (RP-HPLC) using a Waters C-4 column and a buffer gradient of 0.1% TFA in water to 70% acetonitrile in 0.1% TFA in water. The fractions containing pure peptide (determined by analytical HPLC) were combined and the product isolated by lyophilization. Purity of the peptide was better than 95% by HPLC; and amino acid analysis followed by acid hydrolysis (6N HCl, 110° C., 24 hr) gave expected amino acid ratios.

Peptides of the foregoing examples listed below were prepared by the solid phase method.

EXAMPLE 27-01 Ser-Gln-Asn-Phe-Pro-Ile-Val-NH$_2$
EXAMPLE 27-02 Ser-Gln-Asn-Tyr-Pro-Ile-Val-NH$_2$
EXAMPLE 27-03 Ser-Gln-Asn-Tyr-Achx-Ile-Val-NH$_2$
EXAMPLE 27-04 Ser-Gln-Asn-Tyr-Acpr-Ile-Val-NH$_2$
EXAMPLE 27-05 Ser-Gln-Asn-Tyr-Acpnt-Ile-Val-NH$_2$
EXAMPLE 27-06 Thr-Ile-Leu-(beta-Ala)-Leu-Gln-Arg-NH$_2$
EXAMPLE 27-07 Ser-Gln-Asn-Tyr-Pro-Ile-Val-Thr-Leu-Ava-Thr-Gln-Arg-NH$_2$
EXAMPLE 27-15 Ac-Ala-Ala-(D-a-Nal)-Pip-(a-(OH)-Leu)-Val-NH$_2$
EXAMPLE 27-16 Ac-Ala-Ala-Phe-Pip-(a-(OH)-Leu)-Val-NH$_2$
EXAMPLE 27-17 Ac-Ala-Ala-(DL-Phe(4-Cl))-Pip-(a-(OH)-Leu)-Val-NH$_2$
EXAMPLE 27-18 Ala-Ala-Phe-(beta-Ala)-Val-Val-Gly-OH
EXAMPLE 27-19 Ala-Ala-Phe-(beta-Ala)-Nva-Val-Gly-OH
EXAMPLE 27-20 Ala-Ala-Phe-(beta-Ala)-(a-(OH)-iso-Valeryl)-Val-GLy-OH
EXAMPLE 27-21 Ala-Ala-Phe-(beta-Ala)-Val-Val-Gly-OMe
EXAMPLE 27-22 Ala-Ala-Phe-(beta-Ala)-Nva-Val-Gly-OMe
EXAMPLE 27-23 Ala-Ala-Phe-(beta-Ala)-(a-(OH)-iso-Valeryl)-Val-Gly-OMe
EXAMPLE 27-24 Boc-Ala-Ala-Phe-(beta-Ala)-Nva-Gly-OMe
EXAMPLE 27-25 (a,e-dimyristoyl-K)-dP-Ava-Ala-Ala-Phe-Ava-Val-Gly-OMe
EXAMPLE 27-26 Ac-Ala-Ala-(D-a-Nal)-Pip-OMe
EXAMPLE 27-27 Ac-Ala-Ala-(D-a-Nal)-Pip-NHNH$_2$
EXAMPLE 27-28 Ac-Ala-Ala-(L-a-Nal)-Pip-OMe
EXAMPLE 27-29 Ac-Ala-Ala-(L-a-Nal)-Pip-NHNH$_2$
EXAMPLE 27-30 Ac-Ala-Ala-(D-b-Nal)-Pip-OMe
EXAMPLE 27-31 Ac-Ala-Ala-(D-b-Nal)-Pip-NHNH$_2$
EXAMPLE 27-32 Chl-Ala-Ala-(L-a-Nal)-Pip-OMe
EXAMPLE 27-33 Chl-Ala-Ala-(L-a-Nal)-Pip-NHNH$_2$
EXAMPLE 27-34 Paa-Ala-Ala-(D-a-Nal)-Pip-OMe
EXAMPLE 27-36 Ac-Ala-Ala-(DL-Phe(4-Cl))-Pip-OH
EXAMPLE 27-38 Val-Ser-Gln-Asn-Tyr-Pro-Ile-Val-NH$_2$
EXAMPLE 27-39 Val-Ser-Gln-Asn-(D-a-Nal)-Pip-(a-(OH)-Leu)-Val-NH$_2$
EXAMPLE 27-40 i-Boc-(D-Phe)-(D-a-Nal)-Pip-(a-(OH)-Leu)-Val-NH$_2$
EXAMPLE 27-41 (i-Boc-(D-Phe)-Leu-)$_2$-(3,5-di-Aba)-Pro-Leu-(D-Phe)-NH$_2$
EXAMPLE 27-42 (Myristoyl-(D-Phe)-Leu-)$_2$-(3,5-di-Aba)-Pro-Leu-(D-Phe)-NH$_2$
EXAMPLE 27-43 i-Boc-(3,5-di-Aba)-(D-a-Nal)-Pip-(a-(OH)-Leu)-Val-NH$_2$
EXAMPLE 27-46 Pro-Ile-Val-NH$_2$
EXAMPLE 27-47 Ser-Gln-Asn-Tyr
EXAMPLE 27-48 Asn-Phe(CO—CH$_2$N)Pip-Ile-NH$_2$
EXAMPLE 27-49 Quinaldoyl-Asn-Phe(CO—CH$_2$N)Pip-Ile-NH$_2$ EXAMPLE 27-50  Val-Ser-Gln-Asn-Tyr-Pip-Ile-Val-Gln-NH$_2$
EXAMPLE 27-51  Quinaldoyl-Asn-Phe(CHOH—CH$_2$N)Diq-Ile-Val-Gln-NH$_2$
EXAMPLE 27-52  Val-Ser-Gln-Asn-Tyr-Diq-Ile-Val-Gln-NH$_2$
EXAMPLE 27-53  Boc-Asn-Phe(CO—CH$_2$N)Diq-NHtBu
EXAMPLE 27-54  Succinyl-Ser-Gln-Asn-Tyr-Pro-Ile-Val-NH$_2$
EXAMPLE 27-55  Succinyl-Ser-Gln-Asn-Tyr
EXAMPLE 27-56  Quinaldoyl-Asn-Phe(CHOH—CH$_2$N)Pip-Ile-NH$_2$
EXAMPLE 27-60  Phe(CHOH—CH$_2$N)Phe-Ile-Phe-NH$_2$
EXAMPLE 27-61  Phe(CHOH—CH$_2$N)Pro-Ile-Val-NH$_2$
EXAMPLE 27-62  His-Lys-Arg-Ala-Val-Leu-Phe(4-NO$_2$)-Glu-Ala-Nle-Ser-NH$_2$
EXAMPLE 27-69  [D-Phe]-[D-a-Nal]-Pip-[L-a-(OH)-Leu]-Val-NH$_2$
EXAMPLE 27-70  Boc-Phe(CHOH—CH$_2$N)Phe-Ile-Phe-NH$_2$
EXAMPLE 27-71  Boc-Phe(CHOH—CH$_2$N)Pro-Ile-Val-NH$_2$
EXAMPLE 27-74  Succinyl-Phe(CHOH—CH$_2$N)Phe-Ile-Phe-NH$_2$
EXAMPLE 27-77  [D-Phe]-[D-b-Nal]-Pip-[L-a-(OH)-Leu]-Val-NH$_2$
EXAMPLE 27-79  i-Boc-Tyr-Pro-Ile-Gly-OH

EXAMPLE 28

General procedure for the coupling of DMPE-Succinic Acid or DMPE-Succinic acid to peptides containing free amine group EXAMPLE 28F: DPPE-Succinyl-Phe(CHOH—CH$_2$N)Phe-Ile-Phe-NH$_2$
EXAMPLE 28G: DPPE-Succinyl-Phe-O—CH$_2$—CHOH NH$_2$-Phe-O—CH$_2$—CHOH

EXAMPLE 29

Assay For The Reduction of HIV Syncytia Formed In HT4-6C Cells

The syncytia reduction assay as described by Larder, B. et al., *science* 243:1731–1734(1989) was used to measure the antiviral effect of protease inhibitor. A Hela cell line, HT4-6C, expressing the human CD4 receptor on its surface was trypsinized with 0.25% trypsin for 5 min. Cells were centrifuged to remove the residual trypsin, and the cell pellet was resuspended in DMEM with 10% FCS. HeLa cells were plated in 96 well plate (1×10$^5$ cells/well) overnight. Cell cultures were infected with HIV (approx. 100 PFU/well) for one hour. The infected cells were then prepared in stock solutions, and were then two fold diluted in 2% DMEM with 0.5% methylcellulose. 100 μl of each diluted antiviral agent is added into each well of HIV infected cells. The treated cell cultures were incubated in 37° C. CO$_2$ incubator for 24 hours. Plates of HIV-infected cell cultures were fixed with methanol and stained with 1% crystal violet for 10 min., the dye is rinsed off with tap water. Each plate is dried and syncytia were counted. The antiviral effect of protease inhibitor is calculated by 50% syncytia reduction.

Antiviral activities for the compounds of the present invention are summarized in the following table.

| Compound | IC$_{50}$ |
| --- | --- |
| EXAMPLE 27–30:<br>Ac—Ala—Ala—(D-b-Nal)—Pip—OMe | >100 uM |
| EXAMPLE 28A:<br>DPPE—Suc—Ala—Ala—(D-b-Nal)—PiP—OMe | 10 uM |
| EXAMPLE 27–40:<br>i-Boc—(D—Phe)—(D-a-Nal)—Pip—(a-(OH)—Leu)—Val—NH$_2$ | 10 uM |
| EXAMPLE 28E:<br>DPPE-Succinyl-[D—Phe]—[D-a-Nal]—Pip—[L-a-(OH)—Leu]—Val—NH$_2$ | 2 uM |
| EXAMPLE 24:<br>(Boc—Phe—O—CH$_2$—CHOH)$_2$ | 1 uM |
| EXAMPLE 25:<br>(Boc—Val—Phe—O—CH$_2$—CHOH)$_2$ | 3 uM |

DPPE-SUCCINIC ACID or DMPE-Succinic Acid (1 mmol) and the required peptide having a free amine function (1 mmol) were dissolved in DMF (5 ml) and DCC (3 mmol) followed by 1-hydroxybenzotriazole (HOBt; Aldrich Chemical Co., HOBt, MW: 153; 450 mg, 3 mmol) were added. The reaction mixture was stirred for 24 hours at room temperature and the product was purified by silica gel chromatography as described in Example 1.

This procedure was used to prepare the following peptides:
EXAMPLE 28A: DPPE-Suc-Ala-Ala-(D-b-Nal)-Pip-OMe
EXAMPLE 28B: DPPE-Succinyl-Val-Ser-Gln-Asn-Tyr-Pip-Ile-Val-Gln-NH$_2$
EXAMPLE 28C: DMPE-Succinyl-Val-Ser-Gln-Asn-Tyr-Pip-Ile-Val-Gln-NH$_2$
EXAMPLE 28D: DMPE-Succinyl-Val-Ser-Gln-Asn-Tyr-Diq-Ile-Val-Gln-NH$_2$
EXAMPLE 28E: DPPE-Succinyl-[D-Phe]-[D-a-Nal]-Pip-[L-a-(OH)-Leu]-Val-NH$_2$

What is claimed is:

1. A peptide-lipid conjugate selected from the group consisting of:

i-Boc—Tyr—Pro—Ile—Gly—C;

X—Ser—Gln—Asn—Tyr—Pro—Ile—Val—C;

X—Ser—Gln—Asn—Tyr-Acpnt-Ile—Val—C;

X-Succinyl-Ala—Ala—(D-b-Nal)—Pip—C;

X-Succinyl-Val—Ser—Gln—Asn—Tyr—Pip—Ile—Val—Gln—C;

X-Succinyl-Val—Ser—Gln—Asn—Tyr—Pip—Ile—Val—Gln—C;

X-Succinyl-Val—Ser—Gln—Asn—Tyr—Diq—Ile—Val—Gln—C;

X-Succinyl-(D—Phe)—(D-a-Nal)—Pip—(L-a-(OH)—Leu)—Val—C;

X-Succinyl-Phe(CHOH—CH$_2$N)Phe—Ile—Phe—C;

-continued

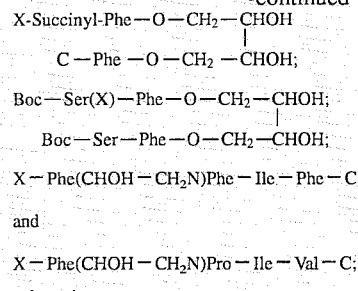

Boc—Ser(X)—Phe—O—CH$_2$—CHOH;

Boc—Ser—Phe—O—CH$_2$—CHOH;

X—Phe(CHOH—CH$_2$N)Phe—Ile—Phe—C;

and

X—Phe(CHOH—CH$_2$N)Pro—Ile—Val—C;

wherein

X represents phosphatidyl-tyrosine; phosphatidyl-serine; phosphatidyl-threonine; phosphatidyl-hydroxyproline; 1-O-alkyl-sn-glycero-3-phospho-O-tyrosine; 1-O-acyl-sn-glycero-3-phospho-O-tyrosine; 1-O-alkyl-sn-glycero-3-phospho-O-serine; 1-O-acyl-sn-glycero-3-phospho-O-serine; 1-O-alkyl-sn-glycero-3 -phospho-O-hydroxyproline; 1-O-acyl-sn-glycero-3-phospho-O-hydroxyproline; 1-O-alkyl-sn-glycero-3-phospho-O-threonine; 1-O-acyl-sn-glycero-3-phospho-O-threonine; 1-O-alkyl-sn-glycero-3-diphospho-O-tyrosine; 1-O-acyl-sn-glycero-3 -diphospho-O-tyrosine; 1-O-alkyl-sn-glycero-3-diphospho-O-serine; 1-O-acyl-sn-glycero-3-diphospho-O-serine; 1-O-alkyl-sn-glycero-3-diphospho-O-hydroxyproline; 1-O-acyl-sn-glycero-3 -diphospho-O-hydroxyproline; 1-O-alkyl-sn-glycero-3-diphospho-O-threonine; 1-O-acyl-sn-glycero-3-diphospho-O-threonine; phosphatidyl ethanolamine-Y; phosphatidic acid, or phosphatidic acid-Z, wherein Y is HOOC—(CH$_2$)$_n$—COOH;

Z is HO—(CH$_2$)$_n$—COOH; and n=1 to 12;

C represents H, OH, OMe, NH$_2$, NH—R where R represents C$_{1-12}$ alkyl, benzyl, substituted benzyl, (CH$_2$)$_n$-phenyl where n=1 to 12, 2-methyl pyridyl, phosphatidyl-tyrosine, phosphatidyl-serine, phosphatidyl-threonine, phosphatidyl-hydroxyproline, 1-O-alkyl-sn-glycero-3-phospho-O-tyrosine, 1-O-acyl-sn-glycero-3-phospho-O-tyrosine, 1-O-alkyl-sn-glycero-3-phospho-O-serine, 1-O-acyl-sn-glycero-3-phospho-O-serine, 1-O-alkyl-sn-glycero-3 -phospho-O-hydroxyproline; 1-O-acyl-sn-glycero-3-phospho-O-hydroxyproline; 1-O-alkyl-sn-glycero-3-phospho-O-threonine, 1-O-acyl-sn-glycero-3-phospho-O-threonine, 1-O-alkyl-sn-glycero-3-diphospho-O-tyrosine, 1-O-acyl-sn-glycero-3 -diphospho-O-tyrosine, 1-O-alkyl-sn-glycero-3-diphospho-O-serine, 1-O-acyl-sn-glycero-3-diphospho-O-serine, 1-O-alkyl-sn-glycero-3-diphospho-O-hydroxyproline, 1-O-acyl-sn-glycero-3-diphospho-O-hydroxyproline, phosphatidyl ethanolamine, or phosphatidyl ethanolamine-W, wherein W is H$_2$N—(CH$_2$)$_n$—COOH, and n=1 to 12.

2. A peptide-lipid conjugate selected from the group consisting of:

5(S)-X-Amino-4(S)-hydroxy-6-phenyl-2 (R)-(phenylmethyl)hexanoyl-Leu-Phe-C;

5(S)-X-Amino-4(S)-hydroxy-6-phenyl-2 (R)-(phenylmethyl)hexanoyl-Leu-C;

5(S)-X-amino-4(S)-hydroxy-6-cyclohexyl-2 (R)-(phenylmethyl)hexanoyl-C;

5(S)-X-Amino-4(R)-hydroxy-6-phenyl-2 (R)-(phenylmethyl)hexanoyl-Leu-Phe-C;

5(S)-X-Amino-4(R)-hydroxy-6-phenyl-2 (R)-(phenylmethyl)hexanoyl-Leu-C; and

5(S)-X-amino-4(R)-hydroxy-6-cyclohexyl-2 (R)-(phenylmethyl)hexanoyl-C; wherein

X represents phosphatidyl-tyrosine; phosphatidyl-serine; phosphatidyl-threonine; phosphatidyl-hydroxyproline; 1-O-alkyl-sn-glycero-3-phospho-O-tyrosine; 1-O-acyl-sn-glycero-3 -phospho-O-tyrosine; 1-O-alkyl-sn-glycero-3-phospho-O-serine; 1-O-acyl-sn-glycero-3-phospho-O-serine; 1-O-alkyl-sn-glycero-3-phospho-O-hydroxyproline; 1-O-acyl-sn-glycero-3-phospho-O-hydroxyproline; 1-O-alkyl-sn-glycero-3-phospho-O-threonine; 1 -O-acyl-sn-glycero-3-phospho-O-threonine; 1-O-alkyl-sn-glycero-3-diphospho-O-tyrosine; 1-O-acyl-sn-glycero-3-diphospho-O-tyrosine; 1-O-alkyl-sn-glycero-3-diphospho-O-serine; 1 -O-acyl-sn-glycero-3-diphospho-O-serine; 1-O-alkyl-sn-glycero-3 -diphospho-O-hydroxyproline; 1-O-acyl-sn-glycero-3-diphospho-O-hydroxyproline; 1-O-alkyl-sn-glycero-3-diphospho-O-threonine; 1-O-acyl-sn-glycero-3-diphospho-O-threonine; phosphatidyl ethanolamine-Y; phosphatidic acid, or phosphatidic acid-Z, wherein Y is HOOC—(CH$_2$)$_n$—COOH and Z is HO—(CH$_2$)$_n$—COOH; and n=1 to 12; and C represents H, OH, OMe, NH$_2$, NH—R where R represents C$_{1-12}$ alkyl, benzyl, substituted benzyl, (CH$_2$)$_n$-phenyl where n=1 to 12, 2-methyl pyridyl, phosphatidyl-tyrosine, phosphatidyl-serine, phosphatidyl-threonine, phosphatidyl-hydroxyproline, 1-O-alkyl-sn-glycero-3 -phospho-O-tyrosine, 1-O-acyl-sn-glycero-3-phospho-O-tyrosine, 1-O-alkyl-sn-glycero-3-phospho-O-serine, 1 -O-acyl-sn-glycero-3-phospho-O-serine, 1-O-alkyl-sn-glycero-3-phospho-O-hydroxyproline; 1-O-acyl-sn-glycero-3 -phospho-O-hydroxyproline; 1-O-alkyl-sn-glycero-3-phospho-O-threonine, 1-O-acyl-sn-glycero-3-phospho-O-threonine, 1-O-alkyl-sn-glycero-3-diphospho-O-tyrosine, 1-O-acyl-sn-glycero-3-diphospho-O-tyrosine, 1-O-alkyl-sn-glycero-3 -diphospho-O-serine, 1-O-acyl-sn-glycero-3-diphospho-O-serine, 1-O-alkyl-sn-glycero-3-diphospho-O-hydroxyproline, 1-O-acyl-sn-glycero-3-diphospho-O-hydroxyproline, 1-O-alkyl-sn-glycero-3-diphospho-O-threonine, 1-O-acyl-sn-glycero-3-diphospho-O-threonine, phosphatidyl ethanolamine, or phosphatidyl ethanolamine-W, wherein W is H$_2$N—(CH$_2$)$_n$—COOH, and n=1 to 12.

3. A peptide-lipid conjugate selected from the group consisting of:

5(S)-X-Amino-4(S)-hydroxy-6-cyclcohexyl-2(R)-isopropyl-hexanoyl-Ile-C;

5(S)-X-Amino-4(R)-hydroxy-6-cyclcohexyl-2(S)-isopropyl-hexanoyl-Ile-C;

5(S)-X-Amino-4(S)-hydroxy-6-phenyl-2(R)-isopropyl-hexanoyl-Ile-C; and

5(S)-X-Amino-4(R)-hydroxy-6-phenyl-2(S)-isopropyl-hexanoyl-Ile-C;

wherein

X represents phosphatidyl-tyrosine; phosphatidyl-serine; phosphatidyl-threonine; phosphatidyl-hydroxyproline; 1 -O-alkyl-sn-glycero-3-phospho-O-tyrosine; 1-O-acyl-sn-glycero-3 -phospho-O-tyrosine; 1-O-alkyl-sn-glycero-3-phospho-O-serine; 1-O-acyl-sn-glycero-3-phospho-O-serine; 1-O-alkyl-sn-glycero-3-phospho-O-hydroxyproline; 1-O-acyl-sn-glycero-3-phospho-O-hydroxyproline; 1-O-alkyl-sn-glycero-3-phospho-O-threonine; 1 -O-acyl-sn-glycero-3-phospho-O-threonine; 1-O-alkyl-sn-glycero-3-diphospho-O-tyrosine; 1-O-acyl-sn-glycero-3-diphospho-O-tyrosine; 1-O-alkyl-sn-glycero-3-diphospho-O-serine;

1-O-acyl-sn-glycero-3-diphospho-O-serine; 1-O-alkyl-sn-glycero-3-diphospho-O-hydroxyproline; 1-O-acyl-sn-glycero-3-diphospho-O-hydroxyproline; 1-O-alkyl-sn-glycero-3-diphospho-O-threonine; 1-O-acyl-sn-glycero-3-diphospho-O-threonine; phosphatidyl ethanolamine-Y; phosphatidic acid, or phosphatidic acid-Z, wherein Y is HOOC—$(CH_2)_n$—COOH and Z is HO—$(CH_2)_n$—COOH; and n=1 to 12; and C represents H, OH, OMe, $NH_2$, NH—R where R represents $C_{1-12}$ alkyl, benzyl, substituted benzyl, $(CH_2)_n$-phenyl where n=1 to 12, 2-methyl pyridyl, phosphatidyl-tyrosine, phosphatidyl-serine, phosphatidyl-threonine, phosphatidyl-hydroxyproline, 1-O-alkyl-sn-glycero-3-phospho-O-tyrosine, 1-O-acyl-sn-glycero-3-phospho-O-tyrosine, 1-O-alkyl-sn-glycero-3-phospho-O-serine, 1-O-acyl-sn-glycero-3-phospho-O-serine, 1-O-alkyl-sn-glycero-3-phospho-O-hydroxyproline; 1-O-acyl-sn-glycero-3-phospho-O-hydroxyproline; 1-O-alkyl-sn-glycero-3-phospho-O-threonine, 1-O-acyl-sn-glycero-3-phospho-O-threonine, 1-O-alkyl-sn-glycero-3-diphospho-O-tyrosine, 1-O-acyl-sn-glycero-3-diphospho-O-tyrosine, 1-O-alkyl-sn-glycero-3-diphospho-O-serine, 1-O-acyl-sn-glycero-3-diphospho-O-serine, 1-O-alkyl-sn-glycero-3-diphospho-O-hydroxyproline, 1-O-acyl-sn-glycero-3-diphospho-O-hydroxyproline, 1-O-alkyl-sn-glycero-3-diphospho-O-threonine, 1-O-acyl-sn-glycero-3-diphospho-O-threonine, phosphatidyl ethanolamine, or phosphatidyl ethanolamine-W, wherein W is $H_2N$—$(CH_2)_n$—COOH, and n=1 to 12.

4. A peptide-lipid conjugate selected from the group consisting of:

(3(S)-X-Asparaginyl)-amino-2(R)-hydroxy-4-phenylbutyl-Pro-C;

(3(S)-X-Asparaginyl)-amino-2(S)-hydroxy-4-phenylbutyl-Pro-C;

(3(S)-X-Asparaginyl)-amino-2(R,S)-hydroxy-4-phenylbutyl-Pro-C;

(3(S)-X-Asparaginyl)-amino-2(R,S)-hydroxy-4-phenylbutyl-Pro-Ile-C;

(3(S)-X-Leucyl-Asparaginyl)-amino-2(R,S)-hydroxy-4-phenylbutyl-Pro-Ile-C;

(3(S)-X-Asparaginyl)-amino-2(R)-hydroxy-4-phenylbutyl-N-1,2,3,4-tetrahydro(R,S)isoquinoline carboxyl-C;

(3(S)-X-Asparaginyl)-amino-2(S)-hydroxy-4-phenylbutyl-N-1,2,3,4-tetrahydro(R,S)isoquinoline carboxyl-C;

(3(S)-X-Asparaginyl)-amino-2(R,S)-hydroxy-4-phenylbutyl-N-1,2,3,4-tetrahydro(R,S)isoquinoline carboxyl-C;

(3(S)-X-Asparaginyl)-amino-2(R,S)-hydroxy-4-phenylbutyl-N-decahydro-3(S)-isoquinoline carboxyl-C;

(3(S)-X-Asparaginyl)-amino-2(R)-hydroxy-4-phenylbutyl-N-decahydro-3(S)-isoquinoline carboxyl-C; and (3(S)-X-Asparaginyl)-amino-2(S)-hydroxy-4-phenylbutyl-N-decahydro-3(S)-isoquinoline carboxyl-C;

wherein

X represents phosphatidyl-tyrosine; phosphatidyl-serine; phosphatidyl-threonine; phosphatidyl-hydroxyproline; 1-O-alkyl-sn-glycero-3-phospho-O-tyrosine; 1-O-acyl-sn-glycero-3-phospho-O-tyrosine; 1-O-alkyl-sn-glycero-3-phospho-O-serine; 1-O-acyl-sn-glycero-3-phospho-O-serine; 1-O-alkyl-sn-glycero-3-phospho-O-hydroxyproline; 1-O-acyl-sn-glycero-3-phospho-O-hydroxyproline; 1-O-alkyl-sn-glycero-3-phospho-O-threonine; 1-O-acyl-sn-glycero-3-phospho-O-threonine; 1-O-alkyl-sn-glycero-3-diphospho-O-tyrosine; 1-O-acyl-sn-glycero-3-diphospho-O-tyrosine; 1-O-alkyl-sn-glycero-3-diphospho-O-serine; 1-O-acyl-sn-glycero-3-diphospho-O-serine; 1-O-alkyl-sn-glycero-3-diphospho-O-hydroxyproline; 1-O-acyl-sn-glycero-3-diphospho-O-hydroxyproline; 1-O-alkyl-sn-glycero-3-diphospho-O-threonine; 1-O-acyl-sn-glycero-3-diphospho-O-threonine; phosphatidyl ethanolamine-Y; phosphatidic acid, or phosphatidic acid-Z, wherein Y is HOOC—$(CH_2)_n$—COOH and Z is HO—$(CH_2)_n$—COOH; and n=1 to 12; and C represents H, OH, OMe, $NH_2$, NH—R where R represents $C_{1-12}$ alkyl, benzyl, substituted benzyl, $(CH_2)_n$-phenyl where n=1 to 12, 2-methyl pyridyl, phosphatidyl-tyrosine, phosphatidyl-serine, phosphatidyl-threonine, phosphatidyl-hydroxyproline, 1-O-alkyl-sn-glycero-3-phospho-O-tyrosine, 1-O-acyl-sn-glycero-3-phospho-O-tyrosine, 1-O-alkyl-sn-glycero-3-phospho-O-serine, 1-O-acyl-sn-glycero-3-phospho-O-serine, 1-O-alkyl-sn-glycero-3-phospho-O-hydroxyproline; 1-O-acyl-sn-glycero-3-phospho-O-hydroxyproline; 1-O-alkyl-sn-glycero-3-phospho-O-threonine, 1-O-acyl-sn-glycero-3-phospho-O-threonine, 1-O-alkyl-sn-glycero-3-diphospho-O-tyrosine, 1-O-acyl-sn-glycero-3-diphospho-O-tyrosine, 1-O-alkyl-sn-glycero-3-diphospho-O-serine, 1-O-acyl-sn-glycero-3-diphospho-O-serine, 1-O-alkyl-sn-glycero-3-diphospho-O-hydroxyproline, 1-O-acyl-sn-glycero-3-diphospho-O-hydroxyproline, 1-O-alkyl-sn-glycero-3-diphospho-O-threonine, 1-O-acyl-sn-glycero-3-diphospho-O-threonine, phosphatidyl ethanolamine, or phosphatidyl ethanolamine-W, wherein W is $H_2N$—$(CH_2)_n$—COOH, and n=1 to 12.

5. A peptide-lipid conjugate selected from the group consisting of:

4(S)-(X-Alanyl)amino-3(S)-hydroxy-5-phenyl-pentanoyl-Val-Val-C;

4(S)-(X-Alanyl-alanyl)amino-3(S)-hydroxy-5-phenyl-pentanoyl-Val-Val-C;

4(S)-(X-Seryl-alanyl-alanyl)amino-3(S)-hydroxy-5-phenyl-pentanoyl-Val-Val-C;

4(S)-(X-Alanyl)amino-3(R)-hydroxy-5-phenyl-pentanoyl-Val-Val-C;

4(S)-(X-Alanyl-alanyl)amino-3(R)-hydroxy-5-phenyl-pentanoyl-Val-Val-C; and

4(S)-(X-Seryl-alanyl-alanyl)amino-3(R)-hydroxy-5-phenyl-pentanoyl-Val-Val-C;

wherein

X represents phosphatidyl-tyrosine; phosphatidyl-serine; phosphatidyl-threonine; phosphatidyl-hydroxyproline; 1-O-alkyl-sn-glycero-3-phospho-O-tyrosine; 1-O-acyl-sn-glycero-3-phospho-O-tyrosine; 1-O-alkyl-sn-glycero-3-phospho-O-serine; 1-O-acyl-sn-glycero-3-phospho-O-serine; 1-O-alkyl-sn-glycero-3-phospho-O-hydroxyproline; 1-O-acyl-sn-glycero-3-phospho-O-hydroxyproline; 1-O-alkyl-sn-glycero-3-phospho-O-threonine; 1-O-acyl-sn-glycero-3-phospho-O-threonine; 1-O-alkyl-sn-glycero-3-diphospho-O-tyrosine; 1-O-acyl-sn-glycero-3-diphospho-O-tyrosine; 1-O-alkyl-sn-glycero-3-diphospho-O-serine; 1-O-acyl-sn-glycero-3-diphospho-O-serine; 1-O-alkyl-sn-glycero-3-diphospho-O-hydroxyproline; 1-O-acyl-sn-glycero-3-diphospho-O-hydroxyproline; 1-O-alkyl-sn-glycero-3-diphospho-O-threonine; 1-O-acyl-sn-glycero-3-diphospho-O-threonine; phosphatidyl ethanolamine-Y; phosphatidic acid, or phosphatidic acid-Z, wherein Y is HOOC—$(CH_2)_n$—COOH and Z is HO—$(CH_2)_n$—COOH; and n=1 to 12; and C represents H, OH, OMe, $NH_2$, NH—R where R represents $C_{1-12}$ alkyl, benzyl, substituted benzyl, $(CH_2)_n$- phenyl where n=1 to 12, 2-methyl pyridyl, phosphatidyl-tyrosine, phosphatidyl-serine, phosphatidyl-threonine, phosphatidyl-hydroxyproline, 1-O-alkyl-sn-glycero-3-phospho-O-tyrosine, 1-O-acyl-sn-glycero-3-phospho-O-tyrosine, 1-O-alkyl-sn-glycero-3-phospho-O-serine, 1-O-acyl-sn-glycero-3-phospho-O-serine, 1-O-alkyl-sn-glycero-3-phospho-O-hydroxyproline; 1-O-acyl-sn-glycero-3-phospho-O-hydroxyproline; 1-O-alkyl-sn-glycero-3-phospho-O-threonine, 1-O-acyl-sn-glycero-3-phospho-O-threonine, 1-O-alkyl-sn-glycero-3-diphospho-O-tyrosine, 1-O-acyl-sn-glycero-3-diphospho-O-tyrosine, 1-O-alkyl-sn-glycero-3-diphospho-O-serine, 1-O-acyl-sn-glycero-3-diphospho-O-serine, 1-O-alkyl-sn-glycero-3-diphospho-O-hydroxyproline, 1-O-acyl-sn-glycero-3-diphospho-O-hydroxyproline, 1-O-alkyl-sn-glycero-3-diphospho-O-threonine, 1-O-acyl-sn-glycero-3-diphospho-O-threonine, phosphatidyl ethanolamine, or phosphatidyl ethanolamine-W, wherein W is $H_2N-(CH_2)_n-COOH$, and n=1 to 12.

6. A peptide-lipid conjugate according to claim 1 selected from the group consisting of:
i-Boc-Tyr-Pro-Ile-Gly-DPPE;
DPPA-Ser-Gln-Asn-Tyr-Pro-Ile-Val-$NH_2$;
DPPA-Ser-Gln-Asn-Tyr-Acpnt-Ile-Val-$NH_2$;
DPPE-Succinyl-Ala-Ala-(D-b-Nal)-Pip-OMe;
DPPE-Succinyl-Val-Ser-Gln-Asn-Tyr-Pip-Ile-Val-Gln-$NH_2$;
DMPE-Succinyl-Val-Ser-Gln-Asn-Tyr-Pip-Ile-Val-Gln-$NH_2$;
DMPE-Succinyl-Val-Ser-Gln-Asn-Tyr-Diq-Ile-Val-Gln-$NH_2$;
DPPE-Succinyl-(D-Phe)-(D-a-Nal)-Pip-(L-a-(OH)-Leu)-Val-$NH_2$;
DPPE-Succinyl-Phe(CHOH—$CH_2$N)Phe-Ile-Phe-$NH_2$;

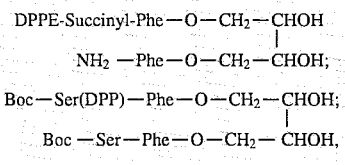

X-Phe(CHOH—$CH_2$N)Phe-Ile-Phe-$NH_2$; and
X-Phe(CHOH—$CH_2$N)Pro-Ile-Val-$NH_2$, wherein DMPE is dimyristoyl phosphatidyl ethanolamine; DPPE is dipalmitoyl ethanolamine; and DPPA is dipalmitoyl phosphatidic acid; and Ser(DPP) is dipalmitoyl phosphatidyl serine.

7. A peptide lipid conjugate of the formula iBoc-Phe-Pip-Val-DPPE.

8. A peptide-lipid conjugate selected from the group consisting of:
X-Val-Phe-Nva-(cyclohexylmethyl(4,4,5,5-tetramethyl-1,3,2-dioxoborlan-2-yl)methylamide;
X-Val-Phe-Nva-(cyclohexylmethyl, dihydroxyboronyl)methylamide;
X-Val-Phe(L-a-Nal)-Nva-(cyclohexylmethyl(4,4,5,5-tetramethyl-1,3,2-dioxoborlan-2-yl)methylamide;
X-Val-Phe(L-a-Nal)-Nva-(cyclohexylmethyl, dihydroxyboronyl)methylamide;
X-Nva(cyclohexylmethyl, dihydroxyboronyl)methylamide; and
X-Val(cyclohexylmethyl, dihydroxyboronyl)methylamide;
wherein:

X represents phosphatidyl-tyrosine; phosphatidyl-serine; phosphatidyl-threonine; phosphatidyl-hydroxyproline; 1-O-alkyl-sn-glycero-3-phospho-O-tyrosine; 1-O-acyl-sn-glycero-3-phospho-O-tyrosine; 1-O-alkyl-sn-glycero-3-phospho-O-serine; 1-O-acyl-sn-glycero-3-phospho-O-serine; 1-O-alkyl-sn-glycero-3-phospho-O-hydroxyproline; 1-O-acyl-sn-glycero-3-phospho-O-hydroxyproline; 1-O-alkyl-sn-glycero-3-phospho-O-threonine; 1-O-acyl-sn-glycero-3-phospho-O-threonine; 1-O-alkyl-sn-glycero-3-diphospho-O-tyrosine; 1-O-acyl-sn-glycero-3-diphospho-O-tyrosine; 1-O-alkyl-sn-glycero-3-diphospho-O-serine; 1-O-acyl-sn-glycero-3-diphospho-O-serine; 1-O-alkyl-sn-glycero-3-diphospho-O-hydroxyproline; 1-O-acyl-sn-glycero-3-diphospho-O-hydroxyproline; 1-O-alkyl-sn-glycero-3-diphospho-O-threonine; 1-O-acyl-sn-glycero-3-diphospho-O-threonine; phosphatidyl ethanolamine-Y; phosphatidic acid, or phosphatidic acid-Z,
wherein Y is HOOC—$(CH_2)_n$—COOH;
Z is HO—$(CH_2)_n$—COOH; and n=1 to 12.

* * * * *